US012364605B2

(12) United States Patent
Keidar et al.

(10) Patent No.: US 12,364,605 B2
(45) Date of Patent: Jul. 22, 2025

(54) CINCHING OF DILATED HEART MUSCLE

(71) Applicant: Edwards Lifesciences Innovation (Israel) Ltd., Caesarea (IL)

(72) Inventors: Yaron Keidar, Kiryat Ono (IL); Nima V. Nia, Mission Viejo, CA (US); Stanton J. Rowe, Corona Del Mar, CA (US); Hengchu Cao, Irvine, CA (US); Tal Reich, Moledet (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 882 days.

(21) Appl. No.: 17/493,654

(22) Filed: Oct. 4, 2021

(65) Prior Publication Data
US 2022/0023047 A1    Jan. 27, 2022

Related U.S. Application Data

(63) Continuation of application No. 16/184,058, filed on Nov. 8, 2018, now Pat. No. 11,135,062.
(Continued)

(51) Int. Cl.
*A61F 2/24* (2006.01)
(52) U.S. Cl.
CPC .... *A61F 2/2487* (2013.01); *A61F 2220/0008* (2013.01); *A61F 2220/0016* (2013.01); *A61F 2250/0004* (2013.01); *A61F 2250/001* (2013.01)
(58) Field of Classification Search
CPC ............ A61F 2/2487; A61F 2220/0008; A61F 2220/0016; A61F 2250/0004; A61F 2250/001
See application file for complete search history.

(56) References Cited

U.S. PATENT DOCUMENTS 1,527,291 A    2/1925    Zorraquin
2,623,521 A    12/1952   Shaw
(Continued)

FOREIGN PATENT DOCUMENTS

CN    113331995 A    9/2021
EP     0611561 A1    8/1994
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Carrie R Dorna
*Assistant Examiner* — Joshua Daryl D Lannu
(74) *Attorney, Agent, or Firm* — Anya Adams

(57) ABSTRACT

Methods, systems, and apparatuses for treating a heart are provided. Methods can include obtaining and using an implant. One or more catheters can be used to properly position and attach the implant in a desired location in a chamber of the heart, for example, such that (i) a first portion of the implant is anchored to a first site on a wall of the chamber, (ii) a second portion of the implant is anchored to a second site on the wall of the chamber, (iii) a mid-portion of the implant extends in a curved path along the wall of the chamber between the first site and the second site, and (iv) an elongate contraction member of the implant cuts across the chamber between the first site and the second site. Other embodiments are described.

24 Claims, 12 Drawing Sheets

Related U.S. Application Data

(60) Provisional application No. 62/588,813, filed on Nov. 20, 2017.

(56) References Cited

U.S. PATENT DOCUMENTS

| | | |
|---|---|---|
| 3,604,488 A | 9/1971 | Wishart et al. |
| 3,656,185 A | 4/1972 | Carpentier |
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,742,829 A | 5/1988 | Law et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,098,388 A | 3/1992 | Kulkashi et al. |
| 5,104,407 A | 4/1992 | Lam et al. |
| 5,108,420 A | 4/1992 | Marks |
| 5,139,485 A | 8/1992 | Smith et al. |
| 5,201,880 A | 4/1993 | Wright et al. |
| 5,226,890 A | 7/1993 | Ianniruberto et al. |
| 5,258,003 A | 11/1993 | Ciaglia et al. |
| 5,258,008 A | 11/1993 | Wilk |
| 5,292,310 A | 3/1994 | Yoon |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,478,329 A | 12/1995 | Ternamian |
| 5,591,191 A | 1/1997 | Kieturakis |
| 5,593,424 A | 1/1997 | Northrup, III |
| 5,601,537 A | 2/1997 | Frassica |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,883 A | 9/1997 | Scarfone et al. |
| 5,669,919 A | 9/1997 | Sanders et al. |
| 5,671,747 A | 9/1997 | Connor |
| 5,676,653 A | 10/1997 | Taylor et al. |
| 5,676,682 A | 10/1997 | Yoon |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup |
| 5,716,370 A | 2/1998 | Williamson et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,755,697 A | 5/1998 | Jones et al. |
| 5,782,844 A | 7/1998 | Yoon et al. |
| 5,810,776 A | 9/1998 | Bacich et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich et al. |
| 5,961,539 A | 10/1999 | Northrup et al. |
| 5,984,959 A | 11/1999 | Robertson et al. |
| 5,993,459 A | 11/1999 | Larsen et al. |
| 6,007,481 A | 12/1999 | Riek et al. |
| 6,012,201 A | 1/2000 | Mitts et al. |
| 6,042,554 A | 3/2000 | Rosenman et al. |
| 6,045,497 A | 4/2000 | Schweich et al. |
| 6,050,936 A | 4/2000 | Schweich et al. |
| 6,059,715 A | 5/2000 | Schweich et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,156,006 A | 12/2000 | Brosens et al. |
| 6,159,240 A | 12/2000 | Sparer et al. |
| 6,165,119 A | 12/2000 | Schweich et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,336 B1 | 4/2001 | Fredriksen |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,293,952 B1 | 9/2001 | Brosens et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larré |
| 6,461,366 B1 | 10/2002 | Seguin |
| 6,470,892 B1 | 10/2002 | Forsell |
| 6,503,274 B1 | 1/2003 | Howanec et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |

(56) References Cited

U.S. PATENT DOCUMENTS

| | | |
|---|---|---|
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,969,354 B1 | 11/2005 | Marian |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,056,294 B2 | 6/2006 | Khairkhahan et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,241,267 B2 | 7/2007 | Furia |
| 7,288,097 B2 | 10/2007 | Séguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,431,726 B2 | 10/2008 | Spence et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Séguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,766,812 B2 | 8/2010 | Schroeder et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |

(56) References Cited

U.S. PATENT DOCUMENTS

| | | |
|---|---|---|
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Bürgler et al. |
| 8,425,402 B2 | 4/2013 | Annest et al. |
| 8,430,926 B2 | 4/2013 | Kirson |
| 8,444,566 B2 | 5/2013 | Agmon |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay et al. |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,500,628 B2 | 8/2013 | Frassica et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,777,841 B2 | 7/2014 | Frassica et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,011,531 B2 | 4/2015 | Rourke et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,259,218 B2 | 2/2016 | Robinson |
| 9,265,608 B2 | 2/2016 | Miller et al. |
| 9,277,994 B2 | 3/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,610,162 B2 | 4/2017 | Zipory et al. |
| 9,622,861 B2 | 4/2017 | Miller et al. |
| 9,636,224 B2 | 5/2017 | Zipory et al. |
| 9,662,209 B2 | 5/2017 | Gross et al. |
| 9,693,865 B2 | 7/2017 | Gilmore et al. |
| 9,713,530 B2 | 7/2017 | Cabiri et al. |
| 9,724,192 B2 | 8/2017 | Sheps et al. |
| 9,730,793 B2 | 8/2017 | Reich et al. |
| 9,775,709 B2 | 10/2017 | Miller et al. |
| 9,788,941 B2 | 10/2017 | Hacohen |
| 9,801,720 B2 | 10/2017 | Gilmore et al. |
| 9,872,769 B2 | 1/2018 | Gross et al. |
| 9,907,547 B2 | 3/2018 | Gilmore et al. |
| 9,937,042 B2 | 4/2018 | Cabiri et al. |
| 9,949,828 B2 | 4/2018 | Sheps et al. |
| 9,968,452 B2 | 5/2018 | Sheps et al. |
| 9,968,454 B2 | 5/2018 | Reich et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |

(56) References Cited

U.S. PATENT DOCUMENTS

| | | |
|---|---|---|
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0106950 A1 | 6/2004 | Grafton et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075723 A1 | 4/2005 | Schroeder et al. |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222488 A1 | 10/2005 | Chang et al. |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259074 A1 | 11/2006 | Kelleher et al. |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |

(56) References Cited

U.S. PATENT DOCUMENTS

| | | |
|---|---|---|
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0203391 A1 | 8/2007 | Bloom et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0265658 A1 | 11/2007 | Nelson et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0249467 A1 | 10/2008 | Burnett et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088678 A1 | 4/2009 | Noda et al. |
| 2009/0088837 A1 | 4/2009 | Gillinov et al. |
| 2009/0093726 A1 | 4/2009 | Takayama et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0118612 A1 | 5/2009 | Grunwald et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0016655 A1 | 1/2010 | Annest et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076408 A1 | 3/2010 | Krever et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0160788 A1 | 6/2010 | Davies et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0274081 A1 | 10/2010 | Okoniewski |
| 2010/0280605 A1* | 11/2010 | Hammer ............ A61B 17/068 623/2.11 |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |

(56) References Cited

U.S. PATENT DOCUMENTS

| | | |
|---|---|---|
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0178537 A1 | 7/2011 | Whitman |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0165735 A1 | 6/2013 | Khairkhahan et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0218206 A1 | 8/2013 | Gadlage |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0245450 A1 | 9/2013 | Prins et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0296902 A1 | 11/2013 | Vonderwalde et al. |
| 2013/0297013 A1 | 11/2013 | Klima et al. |
| 2013/0304093 A1 | 11/2013 | Serina et al. |
| 2013/0310752 A1 | 11/2013 | Kawaura |
| 2013/0331930 A1 | 12/2013 | Rowe et al. |
| 2014/0067054 A1 | 3/2014 | Chau et al. |
| 2014/0081394 A1 | 3/2014 | Keränen et al. |
| 2014/0088368 A1 | 3/2014 | Park |
| 2014/0088646 A1 | 3/2014 | Wales et al. |
| 2014/0094647 A1 | 4/2014 | Schweich, Jr. et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018876 A1 | 1/2015 | Ewers et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0134055 A1 | 5/2015 | Spence et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0335430 A1 | 11/2015 | Loulmet et al. |
| 2015/0351910 A1 | 12/2015 | Gilmore et al. |
| 2016/0008132 A1* | 1/2016 | Cabiri .............. A61B 17/00234 623/2.11 |
| 2016/0015517 A1 | 1/2016 | Sutherland et al. |
| 2016/0029920 A1 | 2/2016 | Kronström et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0270916 A1 | 9/2016 | Cahalane et al. |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0354076 A1 | 12/2016 | Groothuis et al. |
| 2016/0361058 A1 | 12/2016 | Bolduc et al. |
| 2016/0361159 A1 | 12/2016 | Huber |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0135817 A1 | 5/2017 | Tylis et al. |

(56) References Cited

U.S. PATENT DOCUMENTS

| | | |
|---|---|---|
| 2017/0189034 A1 | 7/2017 | Sutherland et al. |
| 2017/0224489 A1 | 8/2017 | Starksen et al. |
| 2017/0245850 A1 | 8/2017 | Call et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1 | 1/2020 | Brauon et al. |
| 2020/0178956 A1 | 6/2020 | Mitelberg et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0052387 A1 | 2/2021 | Greenan et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |
| 2023/0320856 A1 | 10/2023 | Zarbatany et al. |
| 2024/0008985 A1 | 1/2024 | Yuan et al. |
| 2024/0099736 A1 | 3/2024 | Elsheikh et al. |

FOREIGN PATENT DOCUMENTS

| | | |
|---|---|---|
| EP | 0614342 A1 | 9/1994 |
| EP | 1034753 A1 | 9/2000 |
| EP | 3531975 A1 | 9/2019 |
| WO | 9205093 A1 | 4/1992 |
| WO | 1992005093 A1 | 4/1992 |
| WO | 1993010714 A1 | 6/1993 |
| WO | 1996039963 A1 | 12/1996 |
| WO | 1996040344 A1 | 12/1996 |
| WO | 1997001369 A1 | 1/1997 |
| WO | 9846149 A1 | 10/1998 |
| WO | 1998046149 A1 | 10/1998 |
| WO | 1999033414 A1 | 7/1999 |
| WO | 1999063907 A1 | 12/1999 |
| WO | 1999063910 A1 | 12/1999 |
| WO | 2000009048 A1 | 2/2000 |
| WO | 2001056457 A1 | 8/2001 |
| WO | 2002085250 A2 | 10/2002 |
| WO | 02085250 A3 | 2/2003 |
| WO | 03047467 A1 | 6/2003 |
| WO | 2003047467 A1 | 6/2003 |
| WO | 2004012583 A2 | 2/2004 |
| WO | 2005021063 A2 | 3/2005 |
| WO | 2005102181 A1 | 11/2005 |
| WO | 2006116558 A2 | 11/2006 |
| WO | 2007080595 A2 | 7/2007 |
| WO | 2007098512 A1 | 9/2007 |
| WO | 2007136981 A2 | 11/2007 |
| WO | 2008014144 A2 | 1/2008 |
| WO | 2009160631 | 10/2009 |
| WO | 2010000454 A1 | 1/2010 |
| WO | 2010006905 A1 | 1/2010 |
| WO | 2010065274 A1 | 6/2010 |
| WO | 2010128502 A1 | 11/2010 |
| WO | 2011051942 A1 | 5/2011 |
| WO | 2011089401 A1 | 7/2011 |
| WO | 2011089601 A1 | 7/2011 |
| WO | 2011111047 A2 | 9/2011 |
| WO | 2011154942 A2 | 12/2011 |
| WO | 2012011108 A2 | 1/2012 |
| WO | 2012068541 A2 | 5/2012 |
| WO | 2012106346 A1 | 8/2012 |
| WO | 2012176195 A2 | 12/2012 |
| WO | 2013021375 A2 | 2/2013 |
| WO | 2012176195 A3 | 3/2013 |
| WO | 2013078497 A1 | 6/2013 |
| WO | 2014064694 A2 | 5/2014 |
| WO | 2014064964 A1 | 5/2014 |
| WO | 2014087402 A1 | 6/2014 |
| WO | 2014108903 A1 | 7/2014 |
| WO | 2014134624 A1 | 9/2014 |
| WO | 2014195786 A2 | 12/2014 |
| WO | 2015059699 A2 | 4/2015 |
| WO | 2015193728 A2 | 12/2015 |
| WO | 2016059639 A1 | 4/2016 |
| WO | 2016087934 A1 | 6/2016 |
| WO | 2016174669 A1 | 11/2016 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Flato et al., Ultrasound-Guided Venous Cannulation in a Critical Care Unit, Rev. bras. ter. intensiva vol. 21 No. 2 São Paulo Apr./Jun. 2009, pp. 1-11.

Herlambang, et al., Realtime Integral Videography Using Intra-Operative 3-D Ultrasound For Minimally Invasive Heart Surgery.

Agarwal et al. Interventional Cardiology Perspective Functional Tricuspid Regurgitation, Circ Cardiovasc Interv 2009;2;2;565-573 (2009).

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

(56) References Cited

OTHER PUBLICATIONS

Alfieri et al. "Novel Suture Device for Beating-Heart Mitral Leaflet Approximation", Ann Thorac Surg. 2002, 74:1488-1493.
Alfieri, "The edge-to-edge repair of the mitral valve," [Abstract] 6th Annual NewEra Cardiac Care: Innovation&Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
Amplatzer® Cribriform Occluder. A patient guide to Percutaneous, Transcatheter, Atrial Septal Defect Closuer, AGA Medical Corporation, Apr. 2008.
Amplatzer® Septal Occluder. A patient guide to the Non-Surgical Closuer of the Atrial Septal Defect Using the Amplatzer Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, The double-orifice technique as a standardized approach to treat mitral . . . , European Journal of Cardio-thoracic Surgery 17 (2000) 201-205.
Odell JA et al., "Early Results 04yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.
Alfieri et al., "The edge to edge technique," The European Association for Cardio-Thoracic Surgery 14th Annual Meeting Oct. 7-11, Book of Procees. (2000).
Sutton E.E. et al., "Biologically Inspired Catheter for Endovascular Sensing and Navigation", Scientific Reports Journal, vol. 10, 5643, Mar. 27, 2020, DOI https://doi.org/10.1038/s41598-020-62360-w.

* cited by examiner

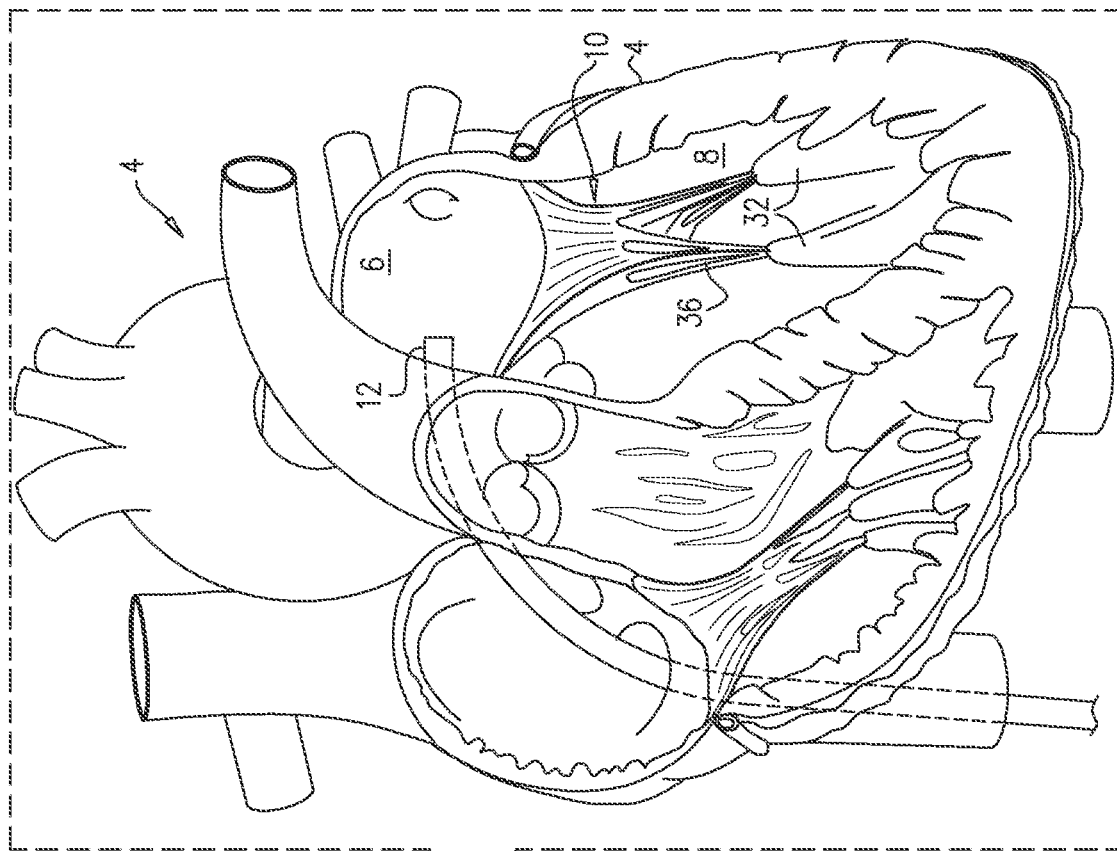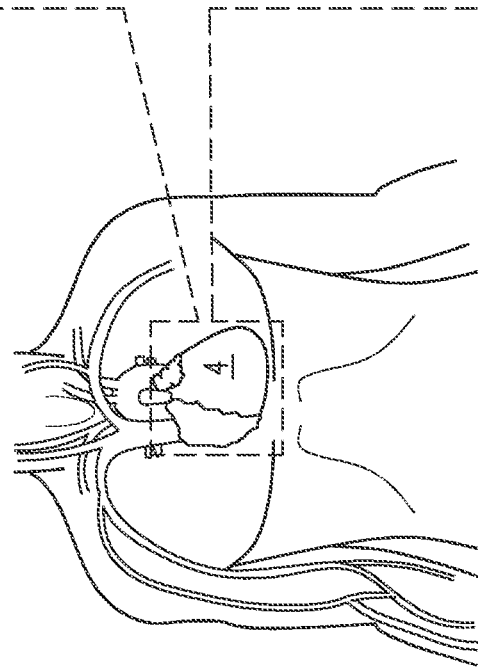
FIG. 1A

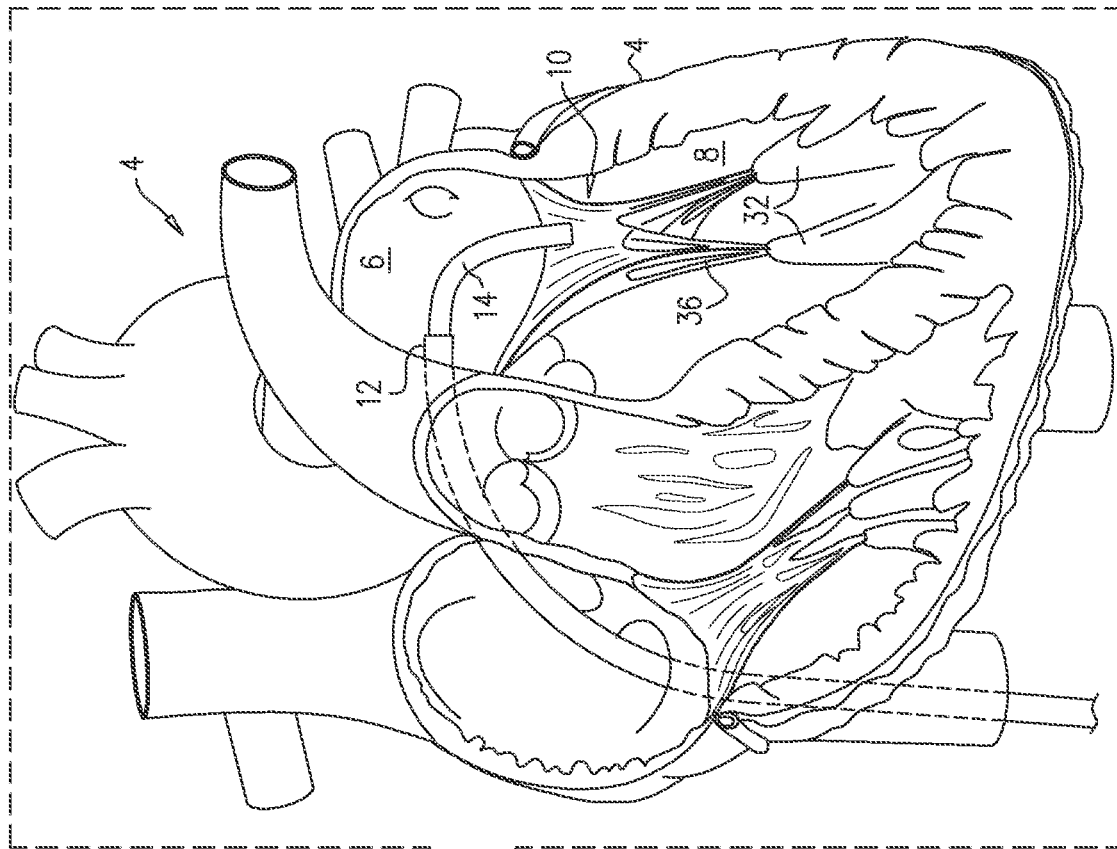
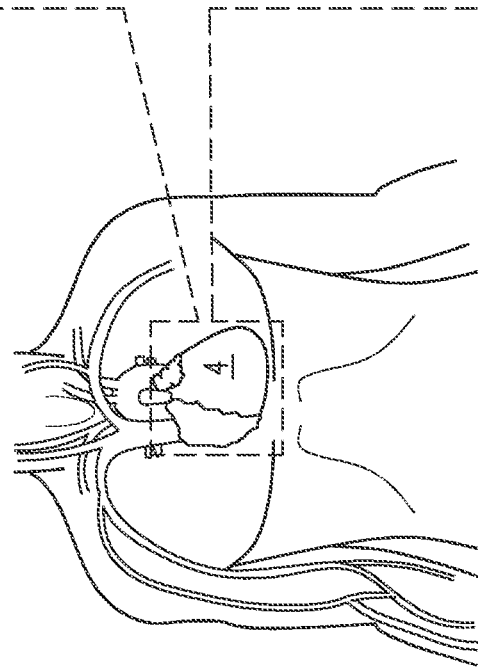
FIG. 1B

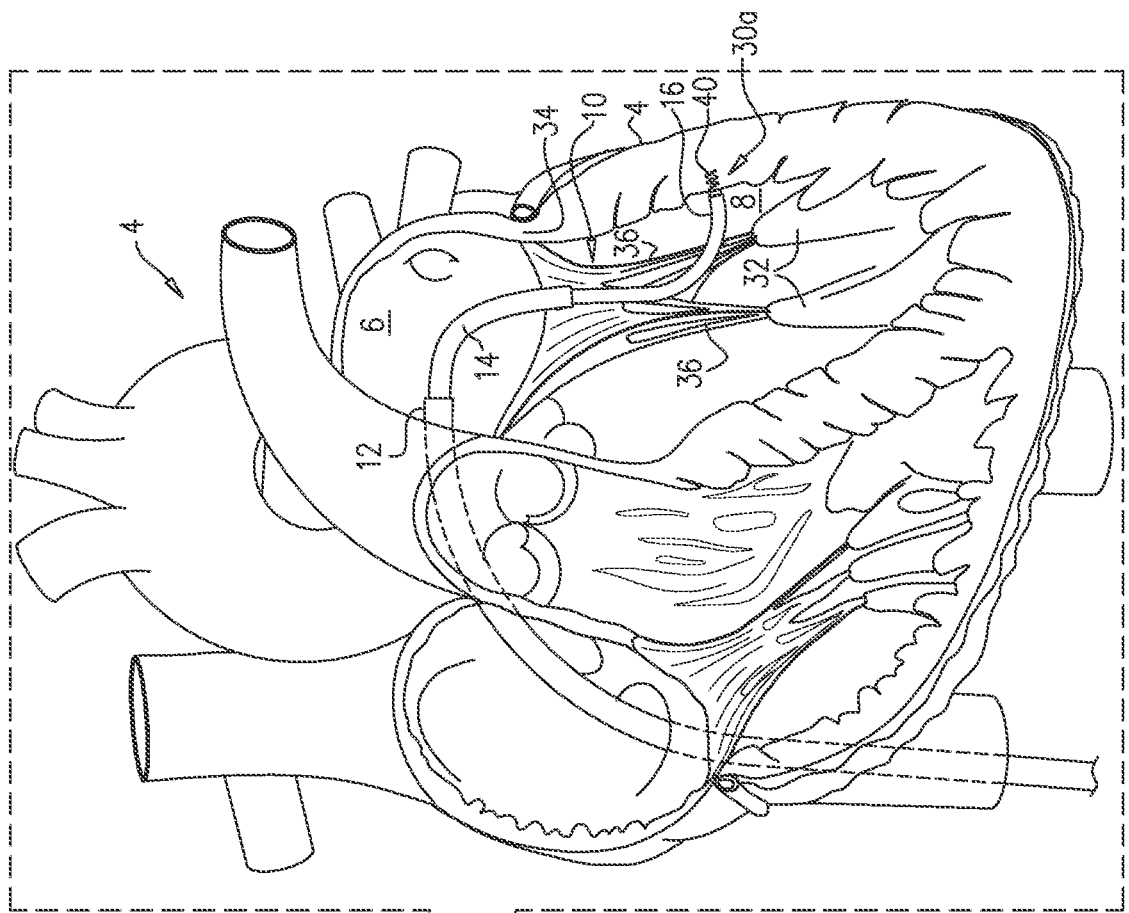
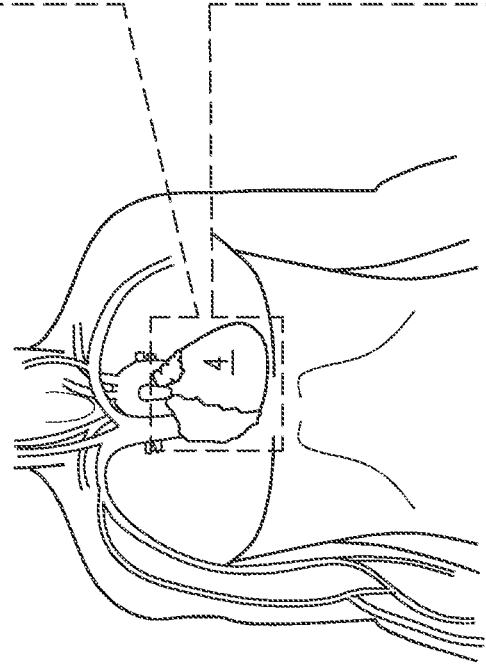
FIG. 1C

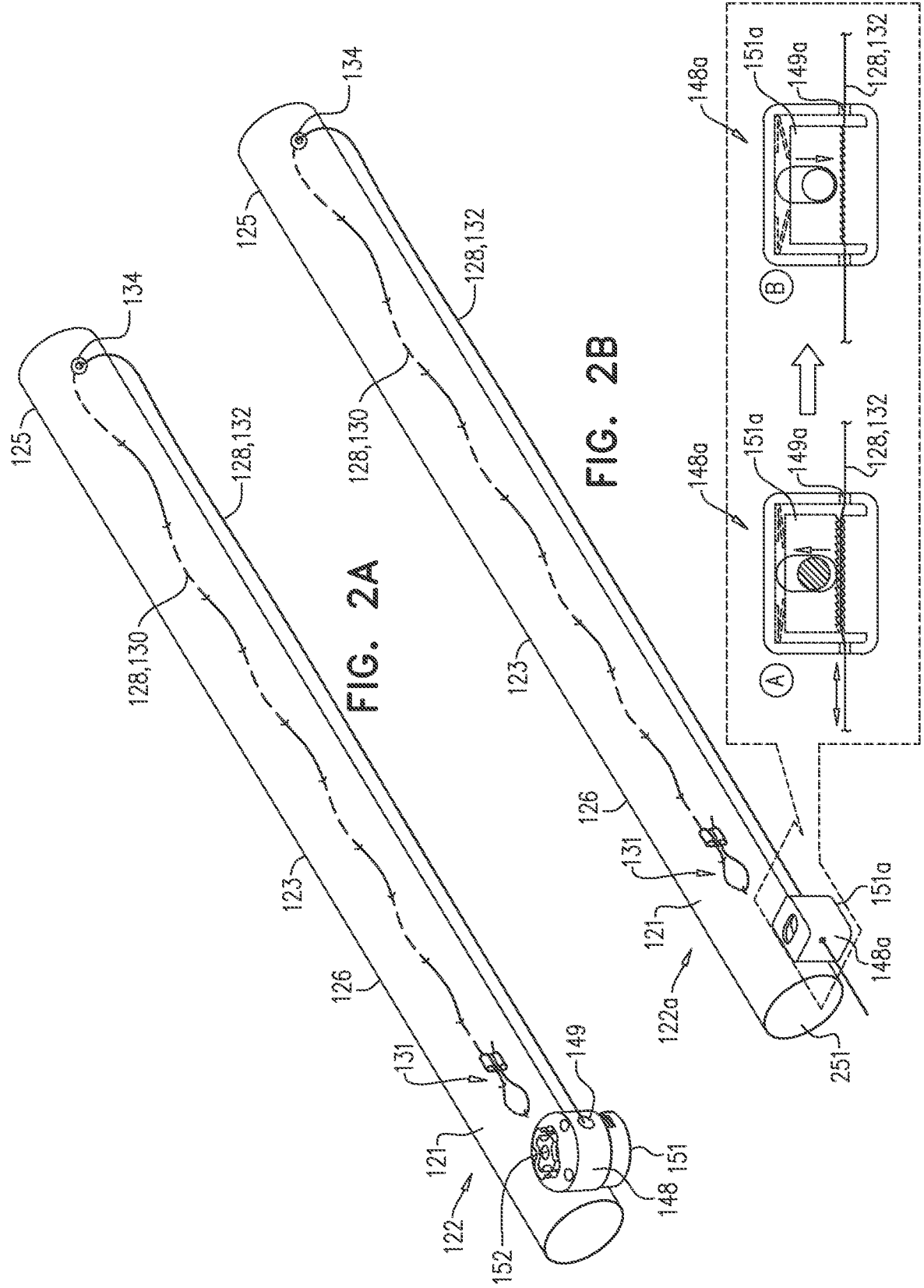

CINCHING OF DILATED HEART MUSCLE

CROSS-REFERENCES TO RELATED APPLICATIONS

The present application is a Continuation of U.S. patent application Ser. No. 16/184,058 to Keidar et al., filed Nov. 8, 2018, which claims benefit of U.S. Provisional Patent Application 62/588,813 to Keidar et al., filed Nov. 20, 2017, and entitled "Cinching of dilated heart muscle," each of which is incorporated herein by reference.

FIELD OF THE INVENTION

Some applications of the present invention relate in general to cardiac repair. For example, some applications of the present invention relate to reshaping the heart or portions thereof.

BACKGROUND

Ischemic heart disease and/or the shape changes of the heart can cause valvular regurgitation (e.g., mitral regurgitation). For example, this can happen by the combination of ischemic dysfunction of the papillary muscles, and the dilatation of the left ventricle that is present in ischemic heart disease, with the subsequent displacement of the papillary muscles and the dilatation of the mitral valve annulus.

Dilatation of the annulus of a native valve (e.g., the mitral valve) can prevent the valve leaflets from fully coapting when the valve is closed or should be closed. Valvular regurgitation can result in increased total stroke volume, decreased cardiac output, and heart weakening. For example, mitral regurgitation of blood from the left ventricle into the left atrium can result in increased total stroke volume and decreased cardiac output, and ultimate weakening of the left ventricle secondary to a volume overload and a pressure overload of the left atrium.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. The description herein relates to systems, assemblies, methods, devices, apparatuses, combinations, etc. that may be utilized for reshaping the heart and/or a portion thereof. Various features and steps as described elsewhere in this disclosure can be included in the examples summarized here.

An implant comprising a flexible sleeve and an elongate contraction member is affixed or anchored to heart tissue (e.g., ventricular tissue), and the contraction member is subsequently tensioned in order to reshape the heart or a chamber of the heart (e.g., a ventricle or atrium).

Methods for use with an implant (e.g., the implant above or any of the implants described elsewhere herein) can include a variety of steps. For example, methods can include, and in at least one application do include, providing or obtaining the implant, which can have (i) an elongate sleeve defining a lumen along a longitudinal axis of the sleeve, and (ii) an elongate contraction member that extends along the sleeve. The methods can be for treating a heart of a subject, the heart having a right atrium, a left atrium, a mitral valve that has an annulus, and/or a left ventricle.

The various methods herein include advancing a distal portion of a catheter (e.g., a delivery catheter/tube) into a chamber of the heart. For example, advancing the distal portion of the catheter transfemorally into the left ventricle, e.g., via the mitral valve. The methods can also include, and in at least one application do include, positioning the distal portion of the catheter such that an open distal end of the catheter faces a first tissue site, the first tissue site being on a wall of a chamber of the heart (e.g., on a ventricular wall of the left ventricle) between a valve annulus and a location remote from the valve annulus (e.g., between a papillary muscle of the left ventricle and the mitral annulus). Positioning the distal portion of the catheter such that the open distal end of the catheter faces the first tissue site can include passing the distal portion of the catheter between two chordae tendineae of the heart.

The methods also include affixing or anchoring a first part of the implant and/or sleeve to the first tissue site, for example, using a first anchor or first attachment means that includes a first tissue-engaging element or portion. This can be done, for example, by passing or driving the first tissue-engaging element through the first part of the implant and/or sleeve and into the first tissue site. Affixing or anchoring the first part of the sleeve can include, and in at least one application does include, affixing or anchoring the first part of the implant and/or sleeve while the catheter remains between the two chordae tendineae.

The methods can include, and in at least one application do include, subsequently, advancing, out of the open distal end of the catheter, a second part of the implant and/or sleeve that is proximal, along the longitudinal axis, from the first part of the implant and/or sleeve, and/or repositioning the distal portion of the catheter such that the open distal end of the catheter faces a second tissue site. The second tissue site can be on a wall of a chamber of the heart (e.g., on a ventricular wall of the left ventricle) between a valve annulus and a location remote from the valve annulus (e.g., between a papillary muscle of the left ventricle and the mitral annulus, or between an annulus and a lower portion of the chamber). Repositioning the distal portion of the catheter can include, and in at least one application does include, repositioning the distal portion of the catheter without capturing a chorda tendinea of the heart between the sleeve and the ventricular wall.

The methods herein also include affixing or anchoring a second part of the implant and/or sleeve to the second tissue site using a second anchor or a second attachment means. The second anchor or second attachment means can have a second tissue-engaging element. The affixing/anchoring can be done by passing or driving the second tissue-engaging element through the second part of the implant and/or sleeve and into the second tissue site. Anchoring the second part of the implant and/or sleeve can include, and in at least one application does include, anchoring the second part of the implant and/or sleeve while the catheter remains between the two chordae tendineae.

The above steps can be repeated with additional parts of the implant and/or sleeve and additional attachment means until the implant and/or sleeve is affixed/anchored to the treatment site as desired. In one application, 2-20 parts of the implant and/or sleeve and 2-20 attachment means or anchors can be used to affix/anchor the implant and/or sleeve to 2-20 tissue sites.

The methods herein also include subsequently, reshaping the heart/chamber or reducing a distance between locations on the heart (e.g., between the papillary muscle and the annulus or annulus and a lower portion of the chamber, etc.), by contracting the implant and/or sleeve. The implant and/or sleeve can be contracted along its length or along the longitudinal axis by applying tension to the contraction member.

The methods herein can include, and in at least one application do include, advancing the first anchor or first attachment means through the catheter to the implant and into the lumen; and subsequently to affixing or anchoring the first part of the sleeve to the first tissue site, advancing the second anchor or second attachment means through the catheter to the implant and into the lumen.

Optionally, the implant can include, and in at least one application does include, a spool, and applying tension to the contraction member can include applying tension to the contraction member by rotating the spool.

The methods herein can further include, and in at least one application do include, subsequently to anchoring or affixing the second part of the sleeve, advancing an adjustment tool through the catheter to the implant. And applying tension to the contraction member can include, and in at least one application does include, applying tension to the contraction member using the adjustment tool.

The methods can further include, and in at least one application do include, identifying the subject as having heart failure with reduced ejection fraction (HFrEF). Further, advancing the distal portion of the catheter transfemorally into the left ventricle via the mitral valve can include, and in at least one application does include, advancing the distal portion of the catheter transfemorally into the left ventricle via the mitral valve responsively to the identifying.

Optionally, the catheter (e.g., delivery catheter) is a third catheter. The distal portion of the catheter can be a distal portion of the third catheter.

Advancing the distal portion of the catheter into the chamber can include, and in at least one application does include, advancing the distal portion of the catheter transfemorally into the left ventricle via the mitral valve. Further, this can include, and in at least one application does include, one or more (or all) of the following: (i) advancing a distal portion of a first catheter into the left atrium, (ii) advancing a distal portion of a second catheter out of the distal portion of the first catheter and into the left ventricle via the mitral valve; and (iii) advancing the distal portion of the third catheter out of the distal portion of the second catheter within the left ventricle. Repositioning the distal portion of the catheter can include, and in at least one application does include, repositioning the distal portion of the third catheter by withdrawing the third catheter into the second catheter.

The second catheter can include, and in at least one application does include, a plurality of second-catheter pull-wires, and advancing the distal portion of the second catheter out of the distal portion of the first catheter and into the left ventricle can include, and in at least one application does include, deflecting the distal portion of the second catheter with respect to the distal portion of the first catheter by tensioning at least one pull-wire of the second-catheter plurality of pull-wires.

The methods herein can further include, and in at least one application do include, rotationally locking the distal portion of the first catheter with respect to the second catheter, wherein deflecting the distal portion of the second catheter includes deflecting the distal portion of the second catheter while the distal portion of the first catheter remains rotationally locked to the second catheter.

The third catheter can include, and in at least one application does include, a plurality of third-catheter pull-wires, and positioning the distal portion of the catheter such that the open distal end of the catheter faces the first tissue site can include deflecting the distal portion of the third catheter with respect to the distal portion of the second catheter by tensioning at least one pull-wire of the plurality of third-catheter pull-wires.

The third catheter can be configured to be rotatable with respect to the second catheter, and the methods can further include, and in at least one application do include, rotating the third catheter with respect to the second catheter while the distal end of the third catheter is disposed in the left ventricle.

The methods herein can further include, and in at least one application do include, rotationally locking the distal portion of the second catheter with respect to the third catheter, and deflecting the distal portion of the third catheter can include, and in at least one application does include, deflecting the distal portion of the third catheter while the distal portion of the second catheter remains rotationally locked to the third catheter.

The first catheter can include, and in at least one application does include, a plurality of first-catheter pull-wires, and the methods can further include, and in at least one application do include, deflecting the distal portion of the first catheter with respect to an immediately-proximal portion of the first catheter by tensioning at least one pull-wire of the plurality of first-catheter pull-wires.

The methods herein can further include, and in at least one application do include, rotationally locking the distal portion of the first catheter with respect to the second catheter, and deflecting the distal portion of the second catheter can include, and in at least one application does include, deflecting the distal portion of the second catheter while the distal portion of the first catheter remains rotationally locked to the second catheter.

Repositioning the distal portion of the catheter such that the open distal end of the catheter faces the second tissue site can include, and in at least one application does include, deflecting again the distal portion of the third catheter with respect to the distal portion of the second catheter by tensioning at least one pull-wire of the plurality of third-catheter pull-wires.

The methods herein can further include, and in at least one application do include, advancing the first anchor to the implant and into the lumen via a channel that extends through the catheter and into the lumen, and anchoring the first part of the sleeve can include, and in at least one application does include, anchoring the first part of the sleeve while a distal end of the channel is disposed at the first part of the sleeve.

The methods herein can further include, and in at least one application do include, partially withdrawing the channel from the lumen such that the distal end of the channel becomes disposed at the second part of the sleeve, and this can be done subsequently to anchoring the first part of the sleeve, and prior to anchoring the second part of the sleeve. Further, anchoring the second part of the sleeve can include, and in at least one application does include, anchoring the second part of the sleeve while the distal end of the channel is disposed at the second part of the sleeve.

For some applications, methods for treating a subject/subject's heart or for use with an implant include providing or obtaining the implant. The implant can be the same as or similar to other implants described in this disclosure, for example, the implant can include (i) an elongate sleeve defining a lumen along a longitudinal axis of the sleeve, and (ii) an elongate contraction member that extends along the sleeve.

The various methods herein can include, and in at least one application do include, one or more or all of the following steps:

advancing a distal portion of a delivery tube/delivery catheter into a chamber of the heart (e.g., left ventricle);

advancing, within the delivery tube, a sleeve to the heart, the sleeve having a first-end portion, a second-end portion, and a mid-portion disposed longitudinally between the first-end portion and the second-end portion;

within the chamber (e.g., ventricle), affixing or anchoring the sleeve in a curved path along a wall (e.g., ventricular wall) of the chamber (e.g., ventricle). This can be done such that an elongate contraction member extends outside of the sleeve between the first-end portion and the second-end portion, and a direct distance between the first-end portion and the second-end portion is shorter than a distance along the sleeve between the first-end portion and the second-end portion;

reshaping the wall of the chamber (e.g., ventricular wall) by reducing the direct distance between the first-end portion and the second-end portion by pulling on the elongate contraction member such that a length of the elongate contraction member that is disposed between the first-end portion and the second-end portion becomes reduced.

Affixing or anchoring the sleeve can include affixing or anchoring the sleeve without capturing a chorda tendinea of the heart between the sleeve and the ventricular wall.

Reducing the direct distance between the first-end portion and the second-end portion can include reducing a radius of curvature of the curved path of the sleeve.

Advancing the delivery tube into the ventricle can include advancing the delivery tube transfemorally to the heart, transseptally into a left atrium of the heart via an interatrial septum of the heart, and into the left ventricle via a mitral valve of the heart.

Advancing the delivery tube into the chamber or ventricle can include advancing the delivery tube transfemorally to the heart, into a right ventricle of the heart via a tricuspid valve of the heart, and transseptally into the left ventricle via an interventricular septum of the heart.

Advancing the delivery tube into the chamber or ventricle can include advancing the delivery tube transapically into the ventricle.

Advancing the sleeve to the heart can include advancing the sleeve within the delivery tube such that, within the delivery tube, the contraction member extends outside and alongside the sleeve, between the first-end portion and the second-end portion.

Affixing or anchoring the sleeve can include affixing or anchoring the first-end portion to an outer wall of the chamber (e.g., a wall opposite the septum or a posterior portion of the ventricular wall), and affixing or anchoring the second-end portion to a septum (e.g., an interventricular septum) of the heart. Optionally, affixing or anchoring the sleeve can include anchoring the mid-portion at an apex of the heart.

In at least one application, affixing or anchoring the sleeve includes affixing/anchoring the first-end portion to a posterior papillary muscle of the heart, and/or affixing/anchoring the second-end portion to an anterior papillary muscle of the heart. Optionally, affixing or anchoring the sleeve can include anchoring the mid-portion circumferentially around the ventricular wall.

Reducing the direct distance between the first-end portion and the second-end portion can include, and in at least one application does include, sliding the contraction member with respect to an end portion selected from the group consisting of: the first-end portion and the second-end portion.

The selected end portion can have a housing coupled thereto. Optionally, the housing can define an eyelet or other opening, and sliding the contraction member can include pulling the contraction member through the eyelet or other opening.

The housing can have a locking component or a locking mechanism coupled thereto. The locking component or locking mechanism can have an unlocked state in which the contraction member is pullable through the eyelet or other opening, and a locked state in which the locking component or locking mechanism inhibits pulling of the contraction member through the eyelet or other opening. Pulling the contraction member through the eyelet or other opening can include, and in at least one application does include, pulling the contraction member through the eyelet while the locking mechanism is in its unlocked state. The methods can further include, and in at least one application do include, subsequently to pulling the contraction member through the eyelet or other opening, transitioning the locking mechanism into its locked state.

Optionally, pulling on the contraction member can include pulling on the contraction member by actuating an adjustment component or mechanism coupled to the sleeve.

Optionally, the adjustment component or adjustment mechanism can include a spool, and actuating the adjustment component or adjustment mechanism can include rotating the spool such that the contraction member collected onto the spool.

The methods can further include, and in at least one application do include, subsequently to anchoring the sleeve, advancing an adjustment tool to the adjustment component or adjustment mechanism, wherein actuating the adjustment component or adjustment mechanism includes using the adjustment tool to actuate the adjustment mechanism.

Affixing or anchoring the sleeve can include, and in at least one application does include, progressively affixing or anchoring a plurality of sleeve-sites of the sleeve to a respective plurality of tissue sites on the wall of the chamber (e.g., on the ventricular wall), the plurality of sleeve-sites being distributed longitudinally along the sleeve, the plurality of sleeve sites including a first sleeve-site and a second sleeve-site, the first-end portion including the first sleeve-site, and the second-end portion including the second sleeve-site. Progressively affixing or anchoring the plurality of sleeve-sites can include, and in at least one application does include, for each sleeve-site of the plurality of sleeve-sites, advancing the sleeve-site out of an open distal end of the delivery tube, and passing or driving, from inside the sleeve, a tissue-engaging element of a respective attachment means or anchor through the sleeve-site and into the respective tissue site. In at least one application, affixing/anchoring involves using 2-20 attachment means or anchors to affix/anchor 2-20 parts of the implant and/or sleeve to 2-20 tissue sites.

Apparatuses and/or implants provided or used herein, e.g., for treating a heart of a subject) can include any of the features or components described with respect to implants in this disclosure, including, for example, a flexible sleeve having a first-end portion and a second-end portion. The flexible sleeve can include a circumferential wall that circumscribes and defines a longitudinal lumen between the first-end portion and the second-end portion.

An apparatus or implant can also include an elongate contraction member.

The elongate contraction member can be configured to define a first region and a second region. The first region can be designed/configured to extend along the sleeve from the first-end portion to the second-end portion, and the second region can be designed/configured to extend, outside of the sleeve, back from the second-end portion to the first-end portion. Optionally, the first region is disposed within the lumen of the sleeve. Alternatively, the first region can weave along the sleeve forming a part of the wall of the sleeve. Optionally, the first region of the contraction member can include a first end of the contraction member, and the second region of the contraction member can include a second end of the contraction member, and the first end of the contraction member can be attached to the first-end portion of the sleeve.

An apparatus or implant herein can optionally include, and in at least one application does include, a housing. The housing can be coupled to the first-end portion of the sleeve and to the contraction member. The housing can be configured to define an eyelet or other opening. The contraction member can be configured to extend through the eyelet or opening such that pulling of the contraction member through the eyelet or opening draws the second-end portion toward the first-end portion by reducing a length of the second region.

An apparatus or implant herein can optionally include, and in at least one application does include, a locking component or a locking mechanism. If the apparatus or implant includes a housing (e.g., similar to the housing described above), the locking component or locking mechanism can be coupled to the housing. The locking component or locking mechanism can have an unlocked state and a locked state. The unlocked state can be a state in which the contraction member is moveable or tensionable (e.g., pullable through the eyelet or opening), and the locked state can be a state in which the locking component or locking mechanism inhibits movement or tensioning (e.g., inhibits pulling of the contraction member through the eyelet). For example, in the unlocked state, the contraction member can be pullable/tensionable to shorten a length of the sleeve between the first-end portion and the second-end portion, and in the locked state, the locking component or locking mechanism inhibits movement of the contraction member relative to the locking component or locking mechanism.

An apparatus or implant herein can further include, and in at least one application do include, an adjustment component or an adjustment mechanism coupled to the contraction member and configured such that actuation of the adjustment component or adjustment mechanism tensions or pulls the contraction member. For example, if it has a housing with an eyelet or opening, it can be configured such that actuation of the adjustment component or adjustment mechanism pulls the contraction member through the eyelet or other opening and into the housing. In an application, the locking mechanism, in the locked state, inhibits actuation of the adjustment component or an adjustment mechanism. In an application, the adjustment component or adjustment mechanism includes a spool, configured such that rotation of the spool pulls the second region of the contraction member through the eyelet and into the housing.

An apparatus or implant herein (or a system including the apparatus or implant), can include, and in at least one application does include, a plurality of anchors. Optionally, each anchor of the plurality of anchors can define or include an anchor head and/or a tissue-engaging element, and can be advanceable through the lumen to a respective sleeve-site of the sleeve. The tissue-engaging element of each anchor can be configured to be driven through the circumferential wall and into tissue (e.g., ventricular tissue) of the heart.

The first region can be slidably coupled to the sleeve, and the pulling of the contraction member (e.g., through the eyelet or opening) slides the first region through the sleeve.

The housing and the contraction member can be arranged with respect the sleeve such that the pulling of the contraction member (e.g., through the eyelet or opening) longitudinally compresses the sleeve.

The contraction member can be slidably coupled to the second-end portion of the sleeve, and the pulling of the contraction member (e.g., through the eyelet or opening) slides the contraction member with respect to the first portion of the sleeve.

The housing can be coupled to the second region of the contraction member, and be arranged such that the second region of the contraction member extends through the eyelet or opening of the housing.

In at least one application, the second region of the contraction member can be pullable through the eyelet or opening such that the second-end portion is drawn toward the first-end portion. The housing can include an adjustment component or an adjustment mechanism coupled to the second region of the contraction member, and be configured such that actuation of the adjustment mechanism pulls the second region (e.g., a portion thereof) of the contraction member through the eyelet or opening and into the housing.

A system herein can include one or more of the components and/or features described above or elsewhere herein. The system can include an implant or apparatus that is the same as or similar to those described above or elsewhere herein. The system can comprise one or more (e.g., three, etc.) steerable catheters for positioning the sleeve within the heart. The system can comprise a delivery catheter for advancing the sleeve into a chamber of the heart.

The present invention will be more fully understood from the following detailed description of applications thereof, taken together with the drawings, in which:

BRIEF DESCRIPTION OF THE DRAWINGS

FIGS. 1A-F are schematic illustrations of an exemplary technique for treating a heart of a subject; and FIGS. 2A-B, 3, 4, 5, 6, and 7 illustrate exemplary schematic illustrations of an implant, and exemplary techniques for implantation thereof, in accordance with some applications of the invention.

DETAILED DESCRIPTION OF EMBODIMENTS

Figure 1D:
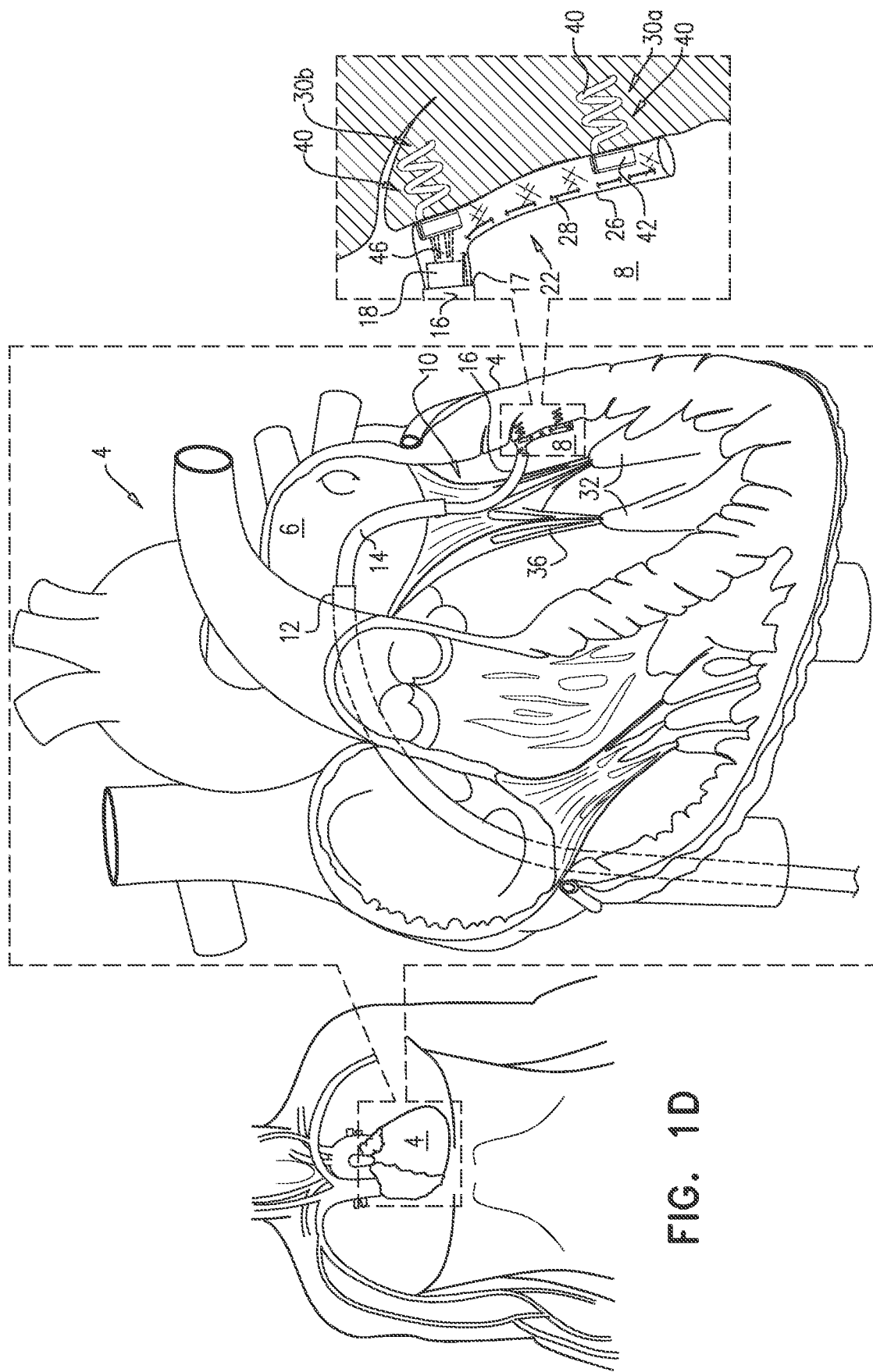

Reference is made to FIGS. 1A-F, which are schematic illustrations of an exemplary technique for treating a heart 4 of a subject. While examples herein are generally given or discussed with respect to treating or reshaping the left ventricle of a heart, the invention is not so limited and the principles, concepts, devices, apparatuses, systems, methods, etc. can be applied to treatment of other locations or regions of the heart or even other parts or organs of the body that may require reshaping.

A catheter 16 is advanced to a desired treatment location in the heart, e.g., a chamber of the heart. For example, catheter 16 can be advanced transfemorally into the left ventricle 8 via the mitral valve 10 (FIGS. 1A-C). Advancement to the treatment location is done using at least one catheter (e.g., a delivery catheter) and can be done using a plurality of catheters. Each catheter used can be steerable or configured to articulate or bend to help steer the system to the desired location.

The catheter or delivery catheter can be advanced to the desired treatment location in a number of different ways, for example, using transfemoral, transseptal, and/or transapical approaches. For some applications, advancement of catheter 16 into the left ventricle is achieved by (i) advancing a distal portion of a first catheter 12 into the left atrium 6 (FIG. 1A), (ii) advancing a distal portion of a second catheter 14 out of the distal portion of first catheter 12 and into left ventricle 8 via the mitral valve (FIG. 1B); and (iii) advancing a distal portion of catheter 16 (i.e., a third catheter) out of the distal portion of catheter 14 within the left ventricle (FIG. 1C). While three catheters are used in the example above, in some embodiments or applications, four catheters can be used. In some embodiments or applications, only two catheters or only one catheter (e.g., delivery catheter 16) can be used.

The distal portion of catheter 16 is positioned such that a distal end 17 (e.g., an open distal end) of the catheter faces a first tissue site, e.g., site 30a (FIG. 1C). For example, first tissue site 30a can be on a wall of a heart chamber, such as a ventricular wall of left ventricle 8 between a papillary muscle 32 and the mitral annulus 34, or between the apex or bottom/lower portion of the chamber and the annulus.

In some applications, implant 22 comprises an elongate flexible sleeve 26 that has a circumferential wall that circumscribes and defines a lumen along a longitudinal axis of the sleeve. In some applications, Implant 22 also comprises an elongate contraction member 28 that extends along the sleeve, e.g., extending through the lumen, being woven into the material of the sleeve, extending through loops on the outside, or otherwise extending along the outside or the inside of the sleeve.

A first part of the implant 22 and/or sleeve 26 is affixed or anchored to first tissue site 30a. This can be done using a variety of attachment means or fastening means, e.g., with anchors, sutures, clips, clamps, staples, adhesive, etc. In one embodiment or application, as shown, this is done using an anchor 40 that includes a coiled or helical tissue-engaging element 44 that can be screwed into tissue, but other types of anchors and tissue-engaging element configurations are also possible. Anchor 40 and anchoring techniques are shown and described in more detail with reference to FIG. 1D.

Subsequently, a second part of implant 22 and/or sleeve 26 that is proximal from the first part of the implant and/or sleeve is advanced out of open distal end 17 of catheter 16, the distal portion of catheter 16 is repositioned such that the open distal end faces a second tissue site 30b, and the second part of the implant and/or sleeve is affixed or anchored to the second tissue site. Again, this can be done using a variety of attachment means. In one embodiment or application, as shown, this is done using a second tissue anchor 40 (FIG. 1D). Second tissue site 30b can also be on the chamber wall, such as on the ventricular wall between papillary muscle 32 and annulus 34.

Optionally, second tissue site 30b can be closer to annulus 34 than is first site 30a. For some such applications, the repositioning of catheter 16 such that the open distal end faces second tissue site 30b can be performed by withdrawing catheter 16 into catheter 14, optionally without changing a degree of bending of the distal portion of catheter 16.

At least two parts of sleeve 26 can be anchored to corresponding tissue sites using corresponding tissue anchors or other attachment/fastening means. However, the above steps can be repeated with additional parts of the implant and/or sleeve and additional attachment means until the implant and/or sleeve is affixed/anchored to the treatment site as desired. In the example shown in the Figures, three parts of sleeve 26 are anchored to three respective tissue sites 30a, 30b, and 30c using three respective anchors 40 (FIG. 1E), but more or additional anchoring sites and anchors or other attachment/fastening means can be used. In one embodiment, 2-20 parts of the implant and/or sleeve and 2-20 attachment means or anchors can be used to affix/anchor the implant and/or sleeve to 2-20 tissue sites.

Each anchor 40 comprises a tissue-engaging element 44 and can comprise an anchor head 42. Tissue-engaging element 44 is shown as a coiled or helical portion that can be screwed or rotated into tissue, but other types of tissue-engaging elements and configurations are also possible. For some applications, the affixing or anchoring is performed by driving tissue-engaging element 44 through a portion of the implant 22, such as the circumferential wall of the corresponding part of sleeve 26 and into the corresponding tissue site. For some applications, a delivery channel 18 extends through catheter 16 and into the lumen of sleeve 26. Each anchor 40 can be delivered sequentially into the lumen of sleeve 26 via channel 18, and can be driven through the wall of the sleeve and into its tissue site using an anchor driver 46. A distal end of channel 18 can be disposed at the part of the sleeve being anchored. Between anchors, channel 18 can be partially withdrawn from the lumen of sleeve 26 such that the distal end of the channel becomes disposed at the next part of the sleeve to be anchored. The distal end of channel 18 can be used to press the part of the sleeve against the corresponding tissue site while the part of the sleeve is being anchored.

Sleeve 26 can be bent at the part of the sleeve being anchored, such that each anchor 40 can be driven in a straight line out of catheter 16 (and channel 18, if present) and through the circumferential wall of the sleeve.

Figure 1E:
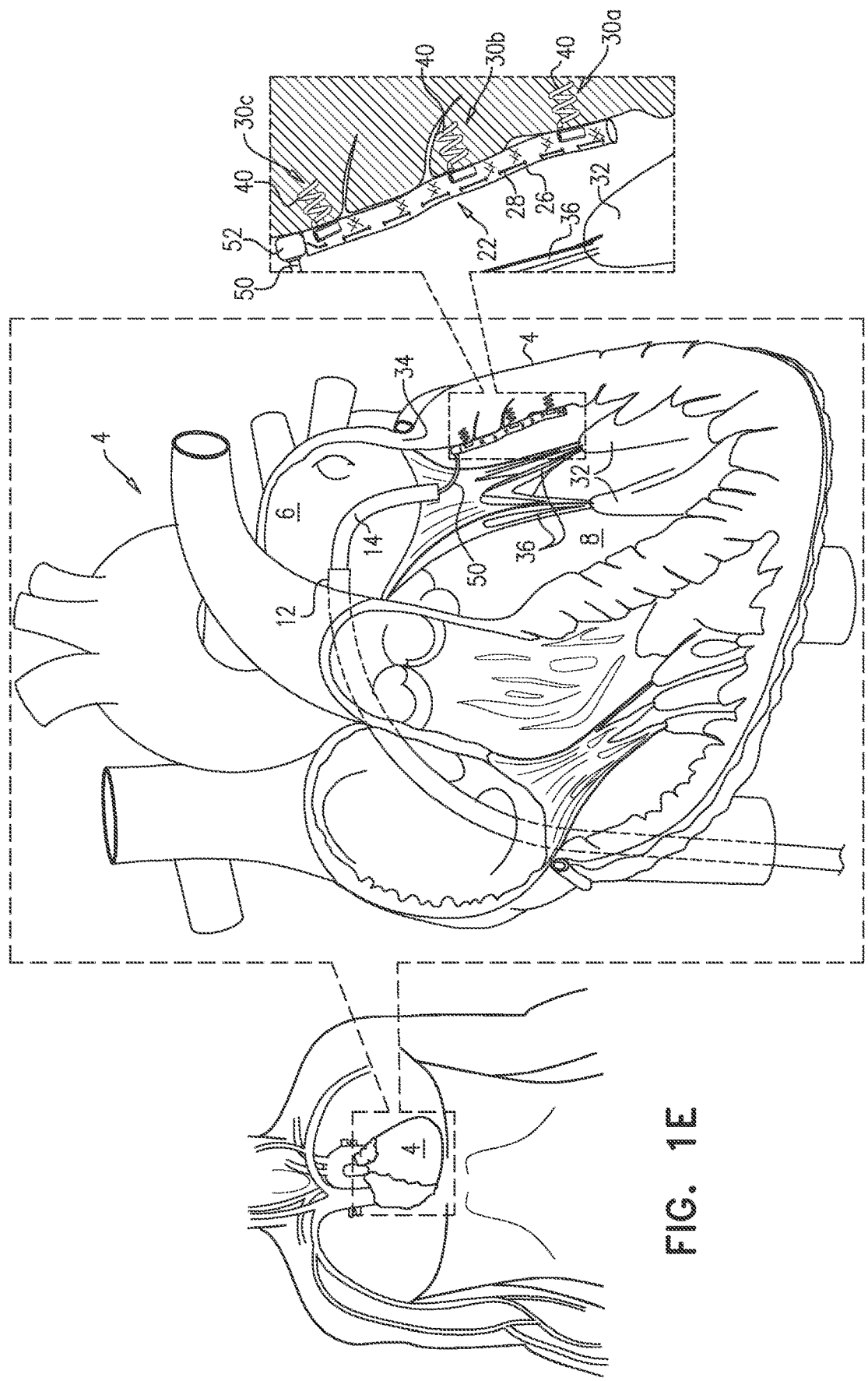
Figure 1F:
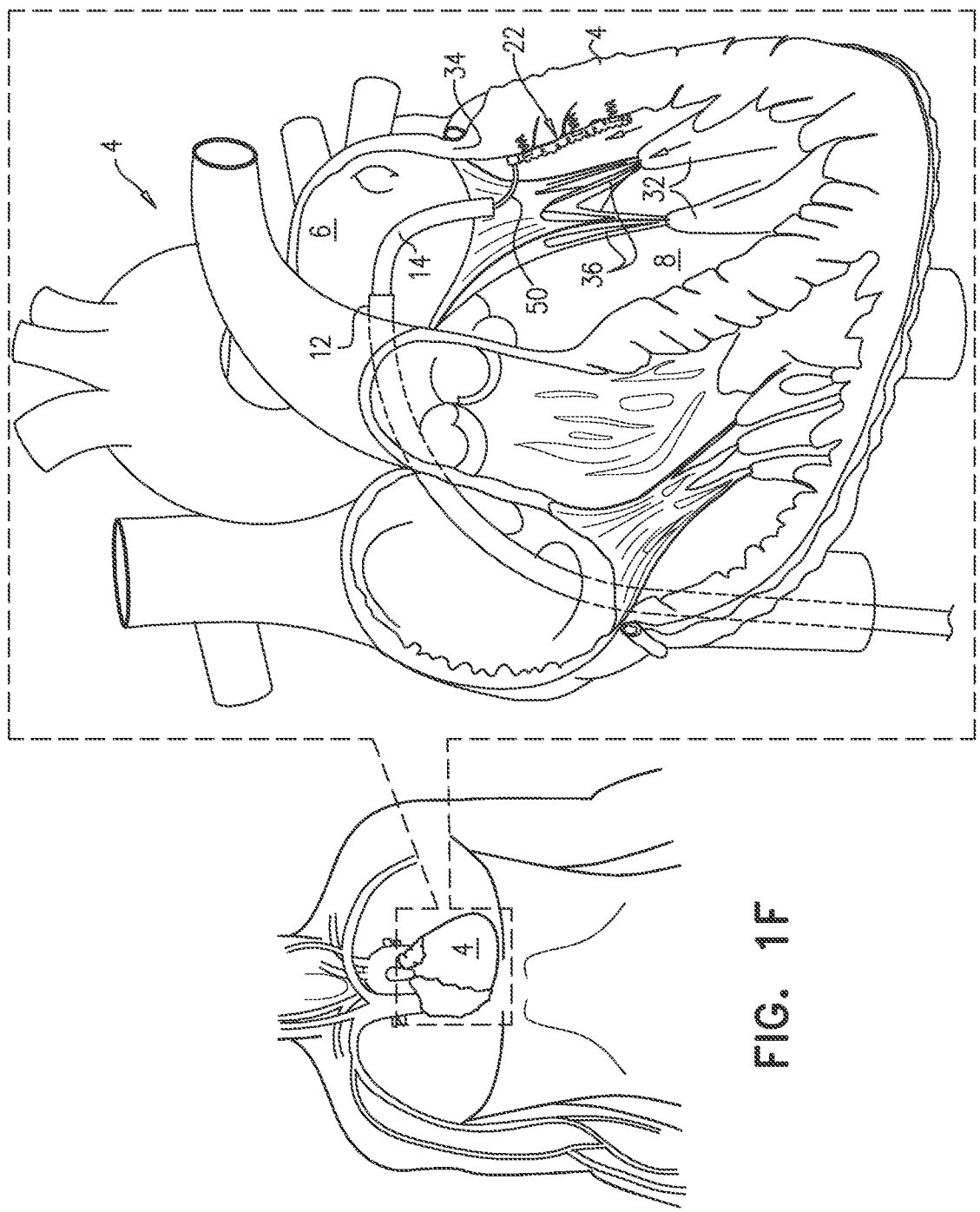

Subsequently, to implantation of implant 22 (i.e., attachment/affixing/anchoring of the parts of implant 22 and/or sleeve 26 to the respective tissue sites), the implant 22 and/or sleeve 26 is contracted or reduced in length/distance from end to end to reshape the surrounding tissue and/or chamber of the heart by applying tension to the contraction member. In one embodiment, a distance between papillary muscle 32 (or lower portion of the chamber) and annulus 34 is reduced by contracting implant 22 and/or sleeve 26 along its longitudinal axis or length by applying tension to contraction member 28 (FIG. 1F).

For some subjects, if the papillary muscles and/or chordae tendineae restrain the leaflets of a native valve too much, this might prevent the leaflets from coming together and/or closing properly. For some subjects, the reduction in the distance between papillary muscle 32 and annulus 34 (e.g., by contracting the implant 22 and/or sleeve 26) may reduce mitral regurgitation by reducing tension and/or allowing the mitral leaflets to move further upstream and together during ventricular systole, thereby improving closure of mitral valve 10. Such subjects may include, for example, subjects with type Mb mitral regurgitation and/or heart failure with reduced ejection fraction (HFrEF). Therefore, for some applications, the technique or methods of treatment include first identifying a subject as having one or more of these conditions.

The application of tension to contraction member 28 is generally achieved using an appropriate tool, such as adjustment tool 50. In FIGS. 1E-F, adjustment tool 50 is shown in contact with implant 22. For some applications, implant 22 can be implanted with adjustment tool 50 pre-coupled to implant 22. For some applications, adjustment tool 50 can be advanced to implant 22 (e.g., via at least one of catheters 12, 14 and 16) subsequent to implantation of the implant. For example, implant 22 can be implanted with a guide member attached, and adjustment tool 50 can be subsequently advanced to the implant along the guide member.

For some applications, implant 22, and the apparatus and techniques for its implantation, are implemented using technology the same as or similar to that described, mutatis mutandis, in one or more of the following publications, which are incorporated herein by reference:

U.S. Pat. No. 9,636,224 to Zipory et al.
U.S. Pat. No. 9,724,192 to Sheps et al.
US patent application publication 2015/0272734 to Sheps et al.

For some applications, implant 22 comprises an adjustment component 52 or other type of adjustment mechanism. For example, tension can be applied to contraction member 28 by actuating the adjustment component or other mechanism using tool 50. For example, adjustment component 52 can comprise a spool, drawstring(s), ratchet, tensioner, etc. Adjustment component 52 or other adjustment mechanism can comprise a lock, locking component, or other locking mechanism that locks a degree of tension of contraction member 28, e.g., by preventing further adjustment of the adjustment component or adjustment mechanism. For example, the lock, etc. may prevent rotation of a spool and/or hold the contraction member at a fixed tension, etc.

Optionally, for some applications, implant 22 may not comprise an actuatable adjustment mechanism as part of the implant, but instead can be contracted just by pulling on contraction member 28. For some such applications, implant 22 can comprise a locking component or mechanism (e.g., a lock, clamp, clip, etc.) that locks a degree of tension of contraction member 28, even in the absence of an actuatable adjustment mechanism.

For some applications, adjustment of implant 22 can be implemented using, alone or in combination, technology that is the same as or similar to that described, mutatis mutandis, in one or more of the following publications, which are incorporated herein by reference:

U.S. Pat. No. 9,636,224 to Zipory et al.
U.S. Pat. No. 9,724,192 to Sheps et al.
US patent application publication 2015/0272734 to Sheps et al.

Implant 22 can be implanted without capturing a chorda tendinea 36 between sleeve 26 and the ventricular wall. For some applications, this can be achieved by passing the distal portion of catheter 16 between two chordae tendineae when positioning the catheter at first tissue site 30a, and not withdrawing the catheter from between the two chordae tendineae until after all anchors 40 have been anchored. That is, the anchoring of all the parts of sleeve 26 can be performed while catheter 16 remains between the two chordae tendineae.

One or more of catheters (e.g., catheters 12, 14, and 16) can comprise one or more (e.g., two, three, four, etc.) pull-wires, and the distal end of the catheter can be deflectable (e.g., "steerable") by tensioning at least one of or one or more of the pull-wires. For example, within left atrium 6, the distal portion of catheter 14 can be deflected with respect to the distal portion of catheter 12. Further, within left ventricle 8, the distal portion of catheter 16 can be deflected with respect to the distal portion of catheter 14. For some applications, the distal portion of catheter 12 can be deflected with respect to a portion of catheter 12 that is proximal (e.g., immediately proximal) to its distal portion, in order to facilitate transseptal access to left atrium 6.

For some applications, the catheters are configured such that the operator can rotationally lock the distal portion of catheter 12 with respect to catheter 14, and the deflecting of the distal portion of catheter 14 can be performed while the distal portion of the first catheter remains rotationally locked to the second catheter.

For some applications, the catheters of the present application, and their steering and locking, may be implemented using, alone or in combination, technology the same as or similar to that described, mutatis mutandis, in one or more of the following publications, which are incorporated herein by reference:

U.S. Pat. No. 9,636,224 to Zipory et al.
U.S. Pat. No. 9,724,192 to Sheps et al.
US patent application publication 2015/0272734 to Sheps et al.

For some applications, the operator can rotationally lock the distal portion of catheter 14 with respect to catheter 16, and the deflecting of the distal portion of catheter 16 can be performed while the distal portion of the first catheter remains rotationally locked to the second catheter. Optionally, catheter 16 can be rotatable with respect to (e.g., within) catheter 14, and the operator can rotate catheter 16 with respect to catheter 14, e.g., while the distal end of catheter 16 is disposed in left ventricle 8, for example, in order to position the open distal end of catheter 16 at the appropriate tissue site.

Reference is made to FIGS. 2A-B, 3, 4, 5, 6, and 7, which are schematic illustrations of an exemplary implant 122, and exemplary techniques for implantation thereof, in accordance with some applications of the invention.

Implant 122 comprises an elongate flexible sleeve 126 that has a circumferential wall that circumscribes and defines a lumen along a longitudinal axis of the sleeve. Implant 122 further comprises a contraction member 128 that can be elongate and extend along the sleeve. Sleeve 126 can be the same as or similar to sleeve 26, mutatis mutandis.

Sleeve 126 has a first-end portion 121, a second-end portion 125, and a mid-portion 123 longitudinally therebetween. The lumen of sleeve 126 can extend between first-end portion 121 and second-end portion 125.

Contraction member 128 can take a variety of shapes and forms. For example, contraction member 128 can be the same as or similar to contraction member 28 described above. In one embodiment or application, contraction member 128 defines a first region 130 and a second region 132. For some applications, first region 130 can extend along sleeve 126 from first-end portion 121 to second-end portion 125, and second region 132 can extend, outside of the sleeve, back from the second-end portion to the first-end portion.

For some applications, and as shown, first region 130 can extend along sleeve 126 by forming part of the circumferential wall and/or weaving in and out along the sleeve (i.e., along the circumferential wall). Alternatively, first region 130 can extend along sleeve 126 by being disposed within the lumen or extending through the lumen.

Implant 122 can comprise a housing 148 that is coupled to first-end portion 121 of sleeve 126, and/or to the contraction member 128. Housing 148 can define an opening or eyelet 149 through which contraction member 128 can extend, such that pulling of the contraction member (e.g., region 132 thereof) through the eyelet can draw second-end portion 125 toward first-end portion 121 by reducing a length of second region 132.

Implant 122 can further comprise a lock, locking device, and/or locking mechanism 151, e.g., coupled to housing 148. Lock or locking device 151 can have an unlocked state in which contraction member 128 is pullable through eyelet 149, and a locked state in which the locking mechanism inhibits pulling of the contraction member through the eyelet.

First region 130 can include a first end 131 of contraction member 128, and second region 132 can include a second end of the contraction member (not visible). Optionally, first end 131 can be attached to the first-end portion of the sleeve, e.g., as shown.

For some applications, implant 122 can comprise an adjustment component 152, or other adjustment mechanism, which can be coupled to second region 132 of contraction member 128, e.g., as shown in FIG. 2A. Adjustment component 152 can be configured such that actuation of adjustment component 152 can pull contraction member 128 (e.g., second region 132 thereof) through eyelet 149 and into housing 148. For some such applications, adjustment component 152 can be disposed within housing 148 and/or can be a component of housing 148. For such applications, lock or locking component 151, in its locked state, can inhibit actuation of the adjustment component or other adjustment mechanism. For some applications, adjustment component 152 and locking component 151 can be implemented using adjustment components or mechanisms and locking components or mechanisms described, mutatis mutandis, in one or more of the following publications, which are incorporated herein by reference:

U.S. Pat. No. 9,636,224 to Zipory et al.
U.S. Pat. No. 9,724,192 to Sheps et al.
US patent application publication 2015/0272734 to Sheps et al.

For some applications, adjustment component 152 comprises a spool, and can be configured such that rotation of the spool pulls second region 132 of contraction member 128 through eyelet 149 and into housing 148 where the spooled-in contraction member is stored on the spool.

FIG. 2B shows an optional embodiment of implant 122—implant 122a. Implant 122a can be identical or similar to implant 122, except where noted. For example, instead of housing 148, implant 122a comprises a housing 148a, which defines an opening or eyelet 149a. Implant 122a does not comprise an adjustment mechanism, and housing 148 does not collect contraction member 128 as it is pulled through eyelet 149a. Rather, contraction member 128 is pulled proximally from a site that is proximal from implant 122a, such that the contraction member is pulled through eyelet 149a and out of a proximal side of housing 148. Instead of locking component 151, implant 122a comprises a locking component 151a, which can engage contraction member 128 directly, rather than inhibiting movement of an adjustment mechanism. FIGS. 3-7 show implant 122 being used as an example, but it is to be noted that implant 122a or another implant can be used instead, mutatis mutandis.

Figure 3:
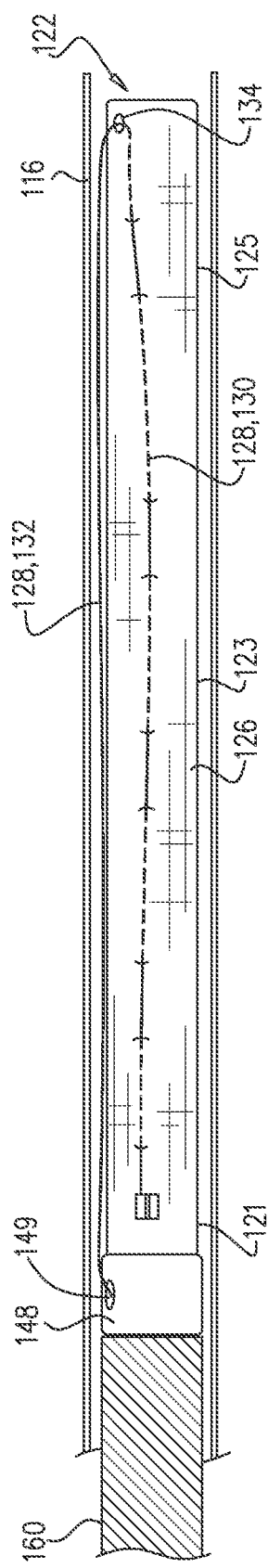

Implant 122 is delivered via a delivery tube/catheter, such as delivery catheter 116. FIG. 3 shows implant 122 in its delivery state, within catheter 116. In the delivery state, region 132 of contraction member 128 can be disposed outside and alongside sleeve 126, and therefore between the sleeve and the wall of catheter 116. For some applications, a deployment tool 160 is used to facilitate movement of implant 122 out of catheter 116, e.g., by providing a reference force as catheter 116 is withdrawn from the implant.

Figure 4:
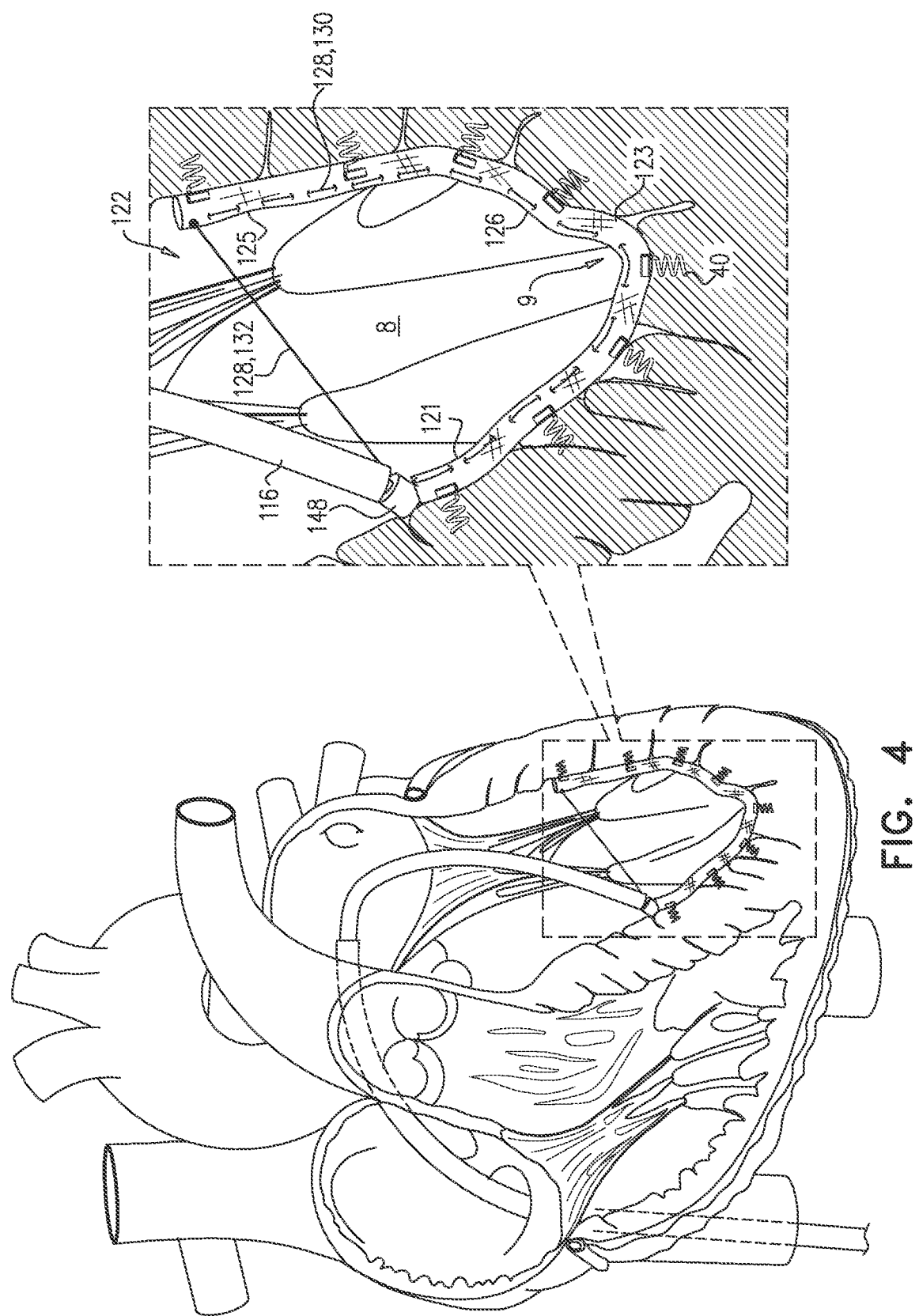
Figure 5:
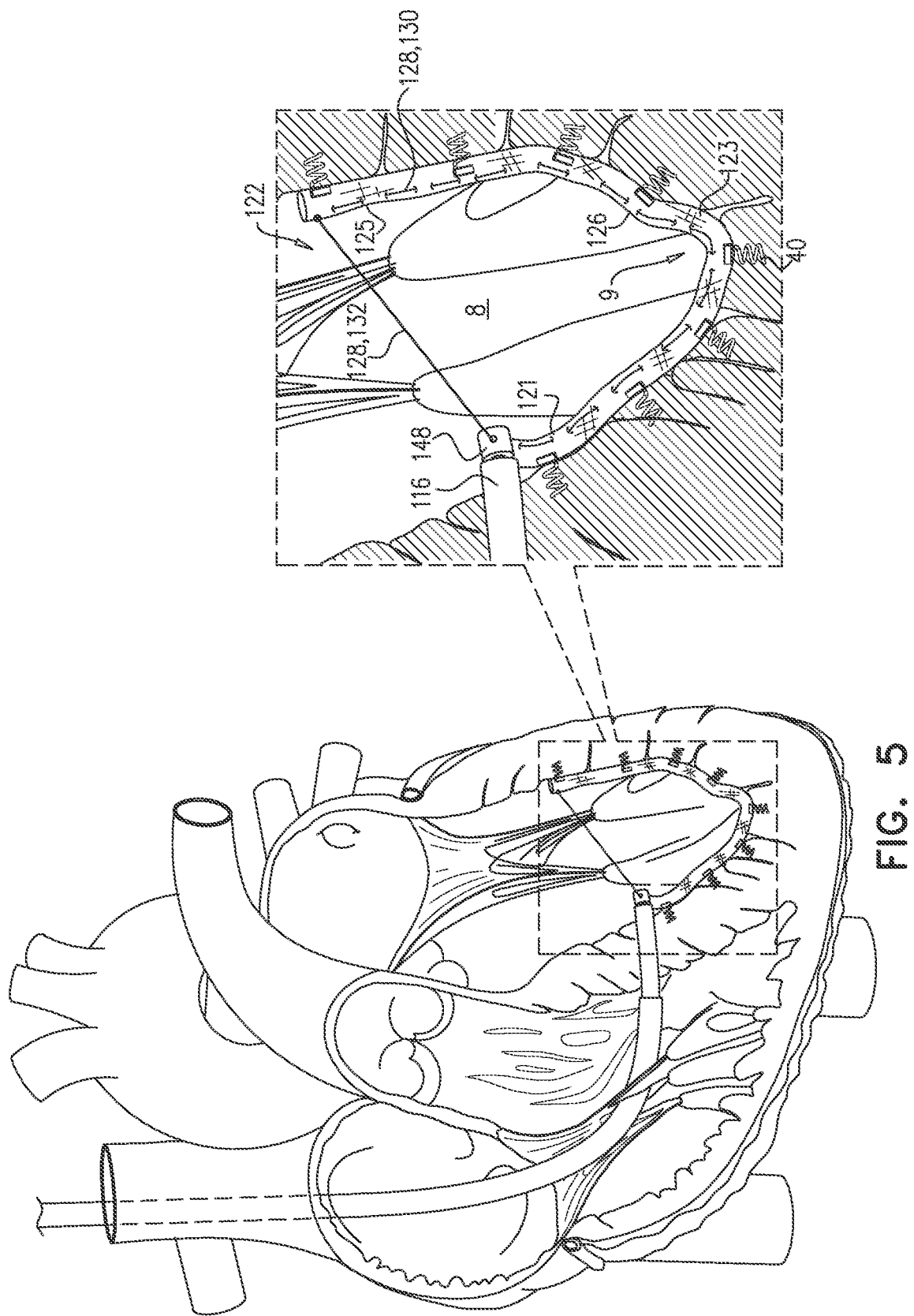

Implant 122 can be implanted in the left ventricle 8 of the heart or in another chamber of the heart, e.g., the right ventricle. Implant 122 can be delivered to the chamber of the heart in a variety of ways, e.g., transfemorally, transapically, and/or transseptally. In one embodiment or application, implant 122 is delivered to the left ventricle 8 via the interatrial septum, e.g., as shown in FIG. 4. In one embodiment or application, implant 122 is delivered to the left ventricle 8 via the interventricular septum, e.g., as shown in FIG. 5. As another option, implant 122 can be delivered by a retrograde approach via the aortic valve (not shown), or transapically (not shown). While examples are given with respect to the left ventricle, the implant, delivery systems, methods, etc. described herein can be adapted for delivery to another chamber of the heart (e.g., left atrium, right atrium, and/or right ventricle) for treatment and/or to modify the shape of the chamber.

Within ventricle 8 (or within another chamber), implant 122 and/or sleeve 126 is affixed or anchored in a curved path along the ventricular wall (or other chamber wall) using an attachment means or anchor such that a direct distance between end portions 121 and 125 is shorter than a distance along the sleeve between the end portions. Sleeve 126 can be affixed/anchored using techniques described hereinabove for sleeve 26, mutatis mutandis. For example, anchors 40 can be sequentially delivered into the lumen of the sleeve, and can be used to progressively anchor respective sleeve-sites along the sleeve. That is, an exemplary method for implanting the sleeve comprises advancing progressively proximal sleeve-sites of the sleeve out of an open distal end of catheter 116, and anchoring (or otherwise fastening/attaching/affixing) the sleeve-sites to respective tissue sites. The plurality of sleeve-sites can include a first sleeve-site within first-end portion 121 and a second sleeve-site within second-end portion 125. As described for sleeve 26, mutatis mutandis, sleeve 126 can be implanted without capturing a chorda tendinea of the heart between the sleeve and the ventricular wall.

Subsequent to the anchoring (or fastening/attachment/affixing), the ventricular wall (or other chamber wall) is reshaped by cinching or contracting the implant by tensioning the contraction member. For some applications, this is done by reducing the direct distance between the first-end portion and the second-end portion by pulling on the elongate contraction member such that a length of the elongate contraction member that is disposed between the first-end portion and the second-end portion becomes reduced (e.g., reducing a radius of curvature of the curved path of the sleeve). As described hereinabove, this can be achieved with or without an adjustment component or adjustment mechanism that is part of the implant. It is believed that such reshaping of the ventricular wall may reduce mitral regurgitation and/or improve ventricular ejection fraction (and reshaping of other chambers/chamber walls may have similar advantages in other chambers).

As described hereinabove for implant 22, mutatis mutandis, implant 122 can be implanted with and adjustment tool attached thereto, or an adjustment tool can be advanced to the implant subsequent to implantation of the implant.

Subsequent to the adjustment, a lock, locking component 151 or other locking mechanism can be transitioned into its locked state, e.g., by releasing an element (not shown) that had been retaining the locking mechanism in its unlocked state.

Figure 6:
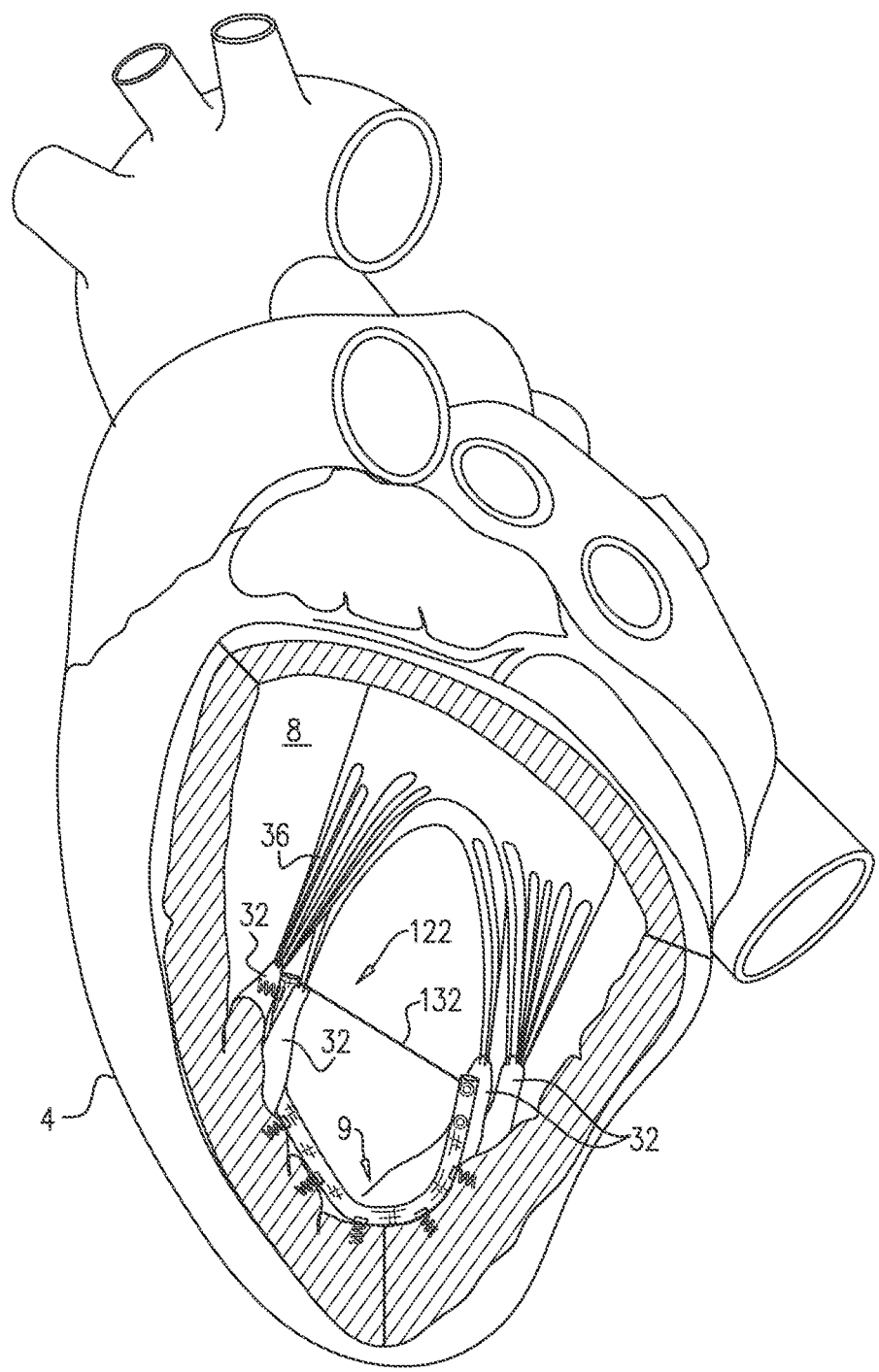
Figure 7:
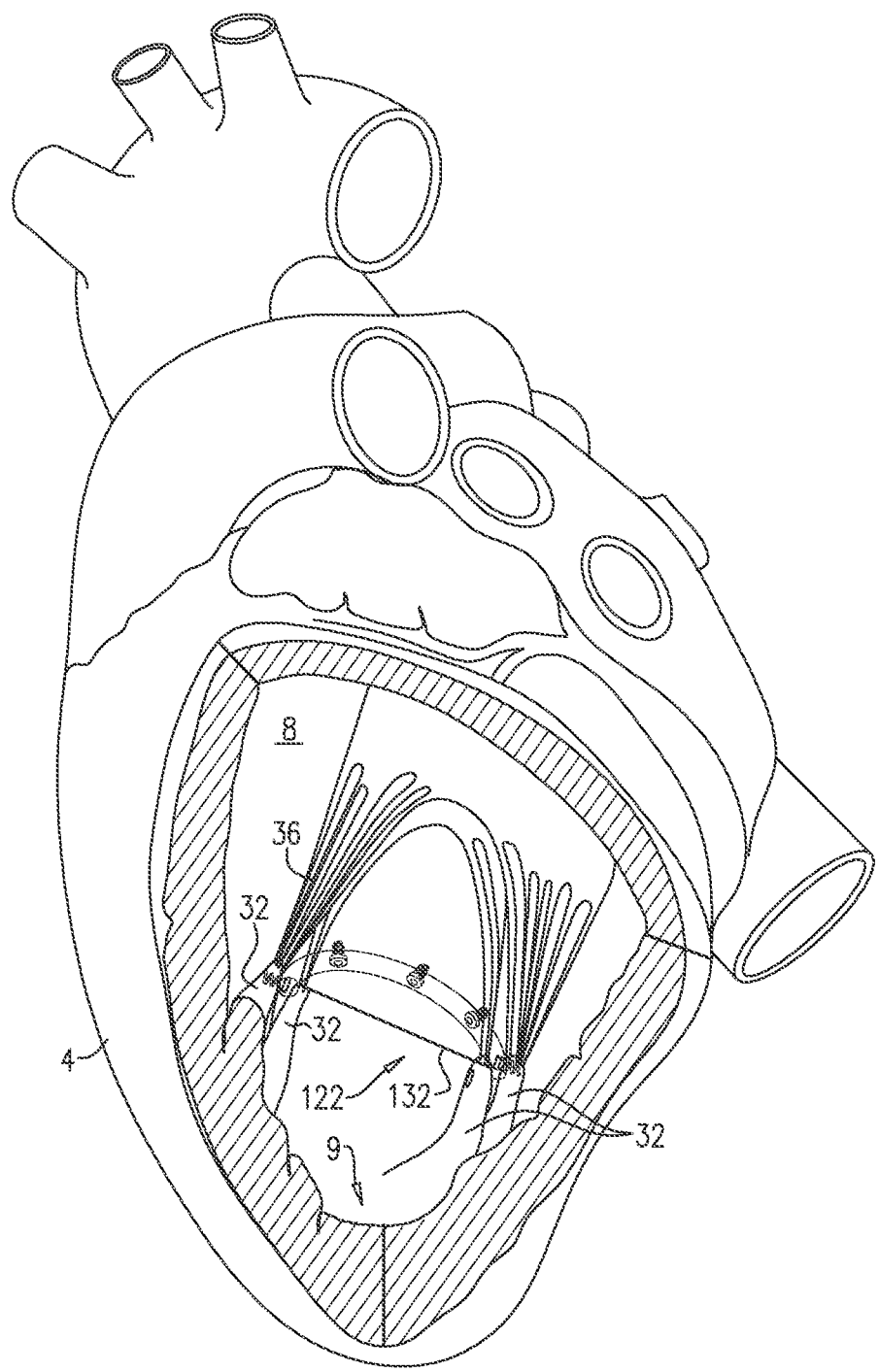

For some applications, one of the end portions can be anchored to a portion of a wall of the chamber, e.g., an outer wall (i.e., non-septum wall), such as a ventricular wall, and the other end portion can be anchored to an interchamber (e.g., interventricular) septum of the heart, e.g., as shown in FIGS. 4 and 5. For some applications, one of the end portions can be anchored to a posterior papillary muscle, and the other end portion can be anchored to an anterior papillary muscle, e.g., as shown in FIGS. 6 and 7. For some applications, mid-portion 123 can be anchored to apex 9 of the heart (i.e., the apical part of ventricle 8), e.g., as shown in FIGS. 4, 5, and 6. For some applications, mid-portion 123 can be anchored higher in the ventricle, such as circumferentially around a lateral part of the ventricular wall, e.g., at the level of the papillary muscles, or even higher, such as shown in FIG. 7, which can allow for cinching the papillary muscles closer to each other. Similar arrangements to the foregoing may be used in other chambers, mutatis mutandis.

It is to be noted that implant 122 can be arranged inversely, with housing 148, locking mechanism 151 and/or adjustment mechanism 152 disposed at second end portion 125. Similarly, implant 122 can be implanted the other way around to that shown or described, i.e., with the position of end portions 121 and 125 reversed.

For some applications, first region 130 can be slidably coupled to sleeve 126, such that the pulling of contraction member 128 through eyelet 149 slides the first region through the sleeve. For such applications, contraction member 128 can be slidably coupled to second-end portion 125 of sleeve 126, and the pulling of the contraction member through opening or eyelet 149 slides the contraction member with respect to the first portion of the sleeve. For example, and as shown, contraction member 128 can exit second-end portion 125 at a second opening or eyelet 134, such that eyelet 134 delimits first region 130 of the contraction member from second region 132 of the contraction member. For such applications, the pulling of contraction member 128 through eyelet 149 can compress sleeve 126 longitudinally. Therefore, for such applications, in addition to reducing the direct distance between end portions 121 and 125, the pulling of contraction member 128 through eyelet 149 can also contract the tissue along the curved path in which sleeve 126 is anchored.

The above systems, platforms, devices, features, aspects, methods, etc. have generally been described with respect to particular embodiments; however, the principles described can be applied to other types of systems, platforms, devices, features, aspects, methods, etc. Further, features described in one embodiment above, including embodiments described in the Summary section, can generally be combined with features described in other embodiments herein. The scope of the present invention includes both combinations and subcombinations of the various features described hereinabove, as well as variations and modifications thereof that are not in the prior art, which would occur to persons skilled in the art upon reading the foregoing description. Methods described separately may be combined. In addition, where methods and steps described above indicate certain events occurring in certain order, the ordering of certain steps can be modified and that such modifications are in accordance with the variations of the invention. Additionally, certain of the steps may be performed concurrently in a parallel process when possible, as well as performed sequentially as described above. Many modifications can be made to adapt a particular situation or device to the teachings of the invention without departing from the essential scope thereof. Therefore, to the extent there are variations of the invention, which are within the spirit of the disclosure or equivalent to the inventions found in the claims, it is the intent that this patent will cover those variations as well.

The invention claimed is:

1. A method for use at a heart of a subject, the method comprising:
    advancing a distal portion of a delivery tube into a chamber of the heart;
    via the delivery tube, advancing an implant to the heart;
    implanting the implant within the chamber such that:
        a first portion of the implant is anchored to a first site on a wall of the chamber,
        a second portion of the implant is anchored to a second site on the wall of the chamber, the implant having a mid-portion disposed longitudinally between the first portion and the second portion,
        the mid-portion extends in a curved path along the wall of the chamber between the first site and the second site, and
        an elongate contraction member of the implant cuts across the chamber between the first site and the second site; and
    subsequently, reshaping the chamber by reducing a direct distance between the first site and the second site by tensioning the elongate contraction member such that a length of the elongate contraction member that cuts across the chamber between the first site and the second site becomes reduced.

2. The method according to claim 1, wherein implanting the implant within the chamber comprises implanting the implant within the chamber without capturing a chorda tendinea of the heart between the implant and the wall of the chamber.

3. The method according to claim 1, wherein reducing the direct distance between the first site and the second site comprises reducing a radius of curvature of the curved path.

4. The method according to claim 1, wherein advancing the distal portion of the delivery tube into the chamber comprises advancing the distal portion of the delivery tube transluminally to the chamber.

5. The method according to claim 4, wherein the chamber is a left ventricle of the heart, and wherein advancing the distal portion of the delivery tube transluminally into the chamber comprises advancing the distal portion of the delivery tube transluminally to a right atrium of the heart, through an interatrial septum of the heart into a left atrium of the heart, and via a mitral valve of the heart into the left ventricle.

6. The method according to claim 4, wherein the chamber is a left ventricle of the heart, and wherein advancing the distal portion of the delivery tube transluminally into the chamber comprises advancing the distal portion of the delivery tube transluminally to a right atrium of the heart, via a tricuspid valve into a right ventricle of the heart, and through an interventricular septum of the heart into the left ventricle.

7. The method according to claim 1, wherein advancing the delivery tube into the chamber comprises advancing the delivery tube transapically into the chamber.

8. The method according to claim 1, wherein advancing the implant to the heart comprises advancing the implant via the delivery tube such that, within the delivery tube, the contraction member extends between the first portion and the second portion.

9. The method according to claim 1, wherein the chamber is a ventricle of the heart, and wherein implanting the implant within the chamber comprises implanting the implant within the ventricle.

10. The method according to claim 9, wherein:
the first site is on a posterior portion of the wall,
the second site is on an interventricular septum of the heart, and
implanting the implant within the chamber comprises implanting the implant such that:
the first portion is anchored to the first site on the posterior portion of the wall, and
the second portion is anchored to the second site on the interventricular septum.

11. The method according to claim 10, wherein implanting the implant comprises implanting the implant such that the mid-portion is anchored at an apex of the heart.

12. The method according to claim 9, wherein:
the first site is on a posterior papillary muscle of the heart,
the second site is on an anterior papillary muscle of the heart, and
implanting the implant within the chamber comprises implanting the implant such that:
the first portion is anchored to the first site on the posterior papillary muscle, and
the second portion is anchored to the second site on the anterior papillary muscle.

13. The method according to claim 12, wherein implanting the implant comprises implanting the implant such that the mid-portion is anchored at an apex of the heart.

14. The method according to claim 12, wherein comprises implanting the implant such that the mid-portion is anchored circumferentially around the wall of the ventricle.

15. The method according to claim 1, wherein reducing the direct distance between the first site and the second site comprises sliding the contraction member with respect to a portion of the implant selected from the group consisting of: the first portion and the second portion.

16. The method according to claim 15, wherein the selected portion has a housing coupled thereto, the housing defining an eyelet, and wherein sliding the contraction member comprises sliding the contraction member through the eyelet.

17. The method according to claim 16, wherein:
the housing has a locking mechanism coupled thereto,
the locking mechanism has an unlocked state in which the contraction member is slidable through the eyelet, and a locked state in which the locking mechanism inhibits sliding of the contraction member through the eyelet,
sliding the contraction member through the eyelet comprises sliding the contraction member through the eyelet while the locking mechanism is in its unlocked state, and
the method further comprises, subsequently to sliding the contraction member through the eyelet, transitioning the locking mechanism into its locked state.

18. The method according to claim 1, wherein tensioning the contraction member comprises tensioning the contraction member by actuating an adjustment mechanism of the implant.

19. The method according to claim 18, wherein the adjustment mechanism includes a spool, and wherein actuating the adjustment mechanism comprises rotating the spool such that the contraction member collected onto the spool.

20. The method according to claim 18, further comprising, subsequently to implanting the implant, advancing an adjustment tool to the adjustment mechanism, wherein actuating the adjustment mechanism comprises using the adjustment tool to actuate the adjustment mechanism.

21. The method according to claim 1, wherein implanting the implant comprises anchoring the mid-portion to the wall of the chamber.

22. The method according to claim 21, wherein anchoring the mid-portion to the wall of the chamber comprises progressively anchoring a series of parts of the mid-portion to the wall of the chamber, the series of parts being distributed longitudinally along the mid-portion.

23. A method for use at a heart of a subject, the method comprising:
anchoring a first portion of an implant to a first site on a wall of a chamber of the heart,
anchoring a second portion of the implant to a second site on the wall of the chamber, the implant having a mid-portion disposed longitudinally between the first portion and the second portion,
anchoring the mid-portion to the wall of the chamber such that:
the mid-portion extends in a curved path along the wall of the chamber between the first site and the second site, and
an elongate contraction member of the implant cuts across the chamber between the first site and the second site; and
subsequently, reshaping the chamber by reducing a direct distance between the first site and the second site by tensioning the elongate contraction member such that a length of the elongate contraction member that cuts across the chamber between the first site and the second site becomes reduced.

24. The method according to claim 23, anchoring the mid-portion to the wall of the chamber comprises progressively anchoring a series of parts of the mid-portion to the wall of the chamber, the series of parts being distributed longitudinally along the mid-portion.

* * * * *